(12) United States Patent
Cuine et al.

(10) Patent No.: US 9,072,781 B2
(45) Date of Patent: Jul. 7, 2015

(54) MORPHINE FORMULATIONS

(71) Applicant: Becton Dickinson France S.A.S., Le Pont de Claix (FR)

(72) Inventors: Alain Cuine, St. Fargeau-Ponthierry (FR); Didier Hoarau, Claix (FR); Pauline Romain, Saint Egreve (FR)

(73) Assignee: Becton, Dickinson France S.A.S., La Pont de Claix (FR)

( * ) Notice: Subject to any disclaimer, the term of this patent is extended or adjusted under 35 U.S.C. 154(b) by 0 days.

(21) Appl. No.: 14/207,245

(22) Filed: Mar. 12, 2014

(65) Prior Publication Data

US 2014/0275144 A1  Sep. 18, 2014

Related U.S. Application Data

(60) Provisional application No. 61/785,218, filed on Mar. 14, 2013.

(51) Int. Cl.

| | | |
|---|---|---|
| *A61K 31/44* | (2006.01) | |
| *A61K 31/485* | (2006.01) | |
| *A01N 43/42* | (2006.01) | |
| *A61K 47/12* | (2006.01) | |
| *A61K 9/00* | (2006.01) | |
| *A61K 47/02* | (2006.01) | |

(52) U.S. Cl.
CPC ............ *A61K 47/12* (2013.01); *A61K 9/0019* (2013.01); *A61K 31/485* (2013.01); *A61K 47/02* (2013.01)

(58) Field of Classification Search
None
See application file for complete search history.

(56) References Cited

U.S. PATENT DOCUMENTS

| | | | |
|---|---|---|---|
| 1,048,712 | A | 12/1912 | Lloyd |
| 2,715,627 | A | 8/1955 | Mehltretter et al. |
| 4,998,400 | A | 3/1991 | Suzuki et al. |
| 5,346,697 | A | 9/1994 | Tokuyama et al. |
| 5,449,745 | A | 9/1995 | Sun et al. |
| 5,624,402 | A | 4/1997 | Imbert |
| 5,650,485 | A | 7/1997 | Sun et al. |
| 5,723,147 | A | 3/1998 | Kim et al. |
| 5,807,572 | A | 9/1998 | Kim et al. |
| 5,881,534 | A | 3/1999 | Ahlqvist et al. |
| 5,891,467 | A | 4/1999 | Willis |
| 5,931,809 | A | 8/1999 | Gruber et al. |
| 5,962,016 | A | 10/1999 | Willis |
| 5,997,899 | A | 12/1999 | Ye et al. |
| 6,007,529 | A | 12/1999 | Gustafsson et al. |
| 6,027,482 | A | 2/2000 | Imbert |
| 6,054,584 | A | 4/2000 | Ma et al. |
| 6,171,613 | B1 | 1/2001 | Ye et al. |
| 6,190,364 | B1 | 2/2001 | Imbert |
| 6,193,998 | B1 | 2/2001 | Ye et al. |
| 6,196,998 | B1 | 3/2001 | Jansen et al. |
| 6,200,627 | B1 | 3/2001 | Lubrecht |
| 6,217,550 | B1 | 4/2001 | Capes |
| 6,241,999 | B1 | 6/2001 | Ye et al. |
| 6,688,468 | B2 | 2/2004 | Waterman |
| 6,743,216 | B2 | 6/2004 | Odell et al. |
| 6,866,142 | B2 | 3/2005 | Lamborne et al. |
| 6,875,400 | B2 | 4/2005 | Speer et al. |
| 7,000,770 | B2 | 2/2006 | Clarke et al. |
| 7,137,968 | B1 | 11/2006 | Burrell et al. |
| 7,141,042 | B2 | 11/2006 | Lubrecht |
| 7,708,719 | B2 | 5/2010 | Wilmot et al. |
| 7,938,580 | B2 | 5/2011 | Gaskell et al. |
| 8,075,535 | B2 | 12/2011 | Carrel et al. |
| 8,652,094 | B2 | 2/2014 | David et al. |
| 2002/0132359 | A1 | 9/2002 | Waterman |
| 2002/0153511 | A1 | 10/2002 | Cotterman et al. |
| 2003/0034264 | A1 | 2/2003 | Hamai et al. |
| 2003/0042166 | A1 | 3/2003 | Waterman |
| 2004/0187438 | A1 | 9/2004 | Clarke et al. |
| 2004/0220545 | A1 | 11/2004 | Heruth et al. |
| 2004/0243214 | A1 | 12/2004 | Farrell et al. |
| 2004/0267194 | A1 | 12/2004 | Sano et al. |
| 2006/0032768 | A1 | 2/2006 | Hamai et al. |
| 2006/0229583 | A1 | 10/2006 | Nagao et al. |
| 2006/0260967 | A1 | 11/2006 | Clarke et al. |
| 2007/0163917 | A1 | 7/2007 | Friesen et al. |
| 2008/0072992 | A1 | 3/2008 | Baleriaux et al. |
| 2008/0249247 | A1 | 10/2008 | Shang et al. |
| 2009/0032426 | A1 | 2/2009 | Tateishi et al. |
| 2009/0281504 | A1 | 11/2009 | Nanba et al. |
| 2010/0326868 | A1 | 12/2010 | McClain et al. |
| 2011/0130717 | A1 | 6/2011 | David et al. |
| 2011/0136847 | A1 | 6/2011 | Chan et al. |

(Continued)

FOREIGN PATENT DOCUMENTS

| | | |
|---|---|---|
| EP | 0622072 | 11/1994 |
| EP | 0837069 A1 | 4/1998 |

(Continued)

OTHER PUBLICATIONS

Fine et al., J Pain Symptom Manage. 2009;38(3):418-425.
Hospira Morphine Label EN-1179, 2006, pp. 1-8.
Feng Sheng Lin et al., Compatibility and stability of Ketorolac Tromethamine and morphine hydrochloride in 0.9% sodium chloride injection. The Pain Clinic, 2007; 19(3): 99-103.
Morphin Merck Tropfen. Bundesverband der Pharmazeutischen Industrie: "Rote Liste 2002", 2002, Rote Liste Service GmbH.
PCT/EP2014/054831 International Search Report and Written Opinion dated May 6, 2014.

(Continued)

*Primary Examiner* — Jason Sims
*Assistant Examiner* — Tori M Strong
(74) *Attorney, Agent, or Firm* — Wilson Sonsini Goodrich & Rosati

(57) ABSTRACT

Provided herein, generally, are pharmaceutical formulations, e.g., injectable pharmaceutical formulations with improved stability, comprising morphine sulfate or a hydrate thereof, and methods of producing and using the same. Also provided herein are kits comprising the formulations, e.g., injectable morphine formulations.

42 Claims, 7 Drawing Sheets

(56) References Cited

U.S. PATENT DOCUMENTS

| | | |
|---|---|---|
| 2012/0143144 A1 | 6/2012 | Young |
| 2013/0081974 A1 | 4/2013 | Hilliard et al. |

FOREIGN PATENT DOCUMENTS

| | | |
|---|---|---|
| EP | 0909555 A1 | 4/1999 |
| EP | 1241110 A1 | 9/2002 |
| EP | 1243524 A2 | 9/2002 |
| EP | 0909555 B1 | 5/2004 |
| EP | 1586347 A1 | 10/2005 |
| EP | 1616549 A1 | 1/2006 |
| EP | 1653930 B1 | 12/2007 |
| EP | 1875889 A1 | 1/2008 |
| EP | 1827283 B1 | 2/2009 |
| EP | 2080501 A1 | 7/2009 |
| JP | 2004-057321 | 2/2004 |
| JP | 2009-154925 | 7/2009 |
| WO | WO94/13328 | 6/1994 |
| WO | WO98/00159 | 1/1998 |
| WO | WO99/22691 | 5/1999 |
| WO | WO00/76507 | 12/2000 |
| WO | WO 2004091623 A1 * | 10/2004 |
| WO | WO2007/022609 | 3/2007 |
| WO | WO2011/004137 | 1/2011 |

* cited by examiner

MORPHINE FORMULATIONS

CROSS-REFERENCE TO RELATED APPLICATIONS

This application claims the benefit of U.S. Application Ser. No. 61/785,218, filed Mar. 14, 2013, which is hereby incorporated by reference in its entirety.

BACKGROUND OF THE INVENTION

Morphine is a narcotic pain reliever widely used to treat moderate to severe pain. It is generally thought that morphine acts as an agonist at the μ-opioid receptor primarily and also the κ- and δ-opioid receptors of the central nervous system. By acting on one or more of these receptors, morphine can cause analgesia and anesthesia as a result of a receptor-mediated central action on pain perception. In addition to analgesia and anesthesia, morphine can provide widely diverse effects including alterations in mood, euphoria and/or feelings of relaxation, dysphoria, drowsiness, decreased gastrointestinal motility, respiratory depression, nausea, vomiting and alterations of the endocrine and autonomic nervous system.

Morphine has been used for a variety of clinical indications. Some examples of such indications include analgesia for treatment of acute and chronic pain due to, for example, cancer or post-operative surgery, anesthesia during surgery and to allay anxiety during acute pulmonary edema. Several delivery routes have been utilized for administering morphine. These routes include oral, rectal, parenteral (injectable) and buccal administration.

SUMMARY OF THE INVENTION

Provided herein are pharmaceutical formulations, e.g., injectable pharmaceutical formulations, comprising morphine sulfate or a hydrate thereof, methods of producing and using the same, and kits comprising the formulations, e.g., injectable morphine formulations.

In one aspect, provided herein is a pharmaceutical formulation, e.g., an injectable pharmaceutical formulation, comprising: (a) morphine, or a salt thereof, or a hydrate thereof; (b) an isotonic agent; (c) a buffering agent with anti-oxidative properties; (d) a chelating agent; (e) a complement to a chelating agent; and (f) water.

In one embodiment of the formulation, the morphine, or a salt thereof, or a hydrate thereof, is selected from anhydrous morphine, morphine hydrochloride, morphine sulfate, morphine tartrate, morphine citrate, morphine acetate, morphine methobromide, morphine hydrobromide, morphine hydroiodide, morphine lactate and morphine bitartrate. In another embodiment, the morphine, or a salt thereof, or a hydrate thereof, is selected from morphine sulfate pentahydrate or morphine hydrochloride.

In another embodiment, the isotonic agent is selected from sodium chloride, calcium chloride, potassium chloride, sodium bicarbonate, sodium lactate, Ringer's solution, dextrose, lactose, mannitol, glucose, glycerine, dextran, Normosol R, saline, Hartmann's solution, and mixtures and combinations thereof. In another embodiment, the isotonic agent is sodium chloride.

In another embodiment, the buffering agent is a di-carboxylic or tri-carboxylic acid. In another embodiment, the buffering agent is citric acid, iso citric acid, aconitic acid, trimesic acid, propane-1,2,3-tricarboxylic acid, fumaric acid, oxalic acid, maleic acid, malonic acid, glutaric acid, succinic acid or tartaric acid, or hydrates thereof. In another embodiment, the buffering agent is citric acid. In another embodiment, the formulation further comprises a conjugate base to the buffering agent. In another embodiment, the buffering agent is in an amount which provides a molar ratio of morphine to the buffering agent from about 0.4 to about 1.3. In another embodiment, the buffering agent is in an amount which provides a molar ratio of morphine to the buffering agent from about 0.4 to about 0.8. In another embodiment, the buffering agent forms a buffer comprised of anhydrous citric acid and hydrates thereof and anhydrous sodium citrate and hydrates thereof. In another embodiment, the buffering agent is in an amount sufficient to provide a pH of from about 2.5 to about 6.5 to the formulation. In another embodiment, the buffering agent is in an amount sufficient to provide a pH of from about 4.5 to about 5.5 to the formulation. In another embodiment, the buffering agent is in an amount sufficient to provide a pH of about 5 to the formulation.

In another embodiment, the chelating agent is selected from edetic acid, ethylene glycol tetraacetic acid, ethylenediamine, diethylene triamine pentaacetic acid, N-(hydroxyethyl) ethylenediaminetriacetic acid, aminotriacetic acid, 2,3-dimercapto-1-propanesulfonic acid, dimercaptosuccinic acid, dimercaprol, 1,2-bis(o-aminophenoxy)ethane-N,N,N',N'-tetraacetic acid, salts and hydrates thereof. In another embodiment, the chelating agent is edetic acid. In another embodiment, the complement to chelating agent is a calcium salt. In another embodiment, the complement to chelating agent is calcium chloride dihydrate.

In another embodiment, the formulation provides a unit dose of morphine, or a salt thereof, or a hydrate thereof, from about 2 mg/mL to about 15 mg/mL. In another embodiment, the formulation provides a unit dose of morphine, or a salt thereof, or a hydrate thereof, from about 2 mg/mL to about 10 mg/mL.

In certain embodiments, the formulation provided herein comprises per mL (a) from about 2 mg to about 15 mg of morphine sulfate pentahydrate; (b) an isotonic agent; (c) a buffering agent in an amount which provides a molar ratio of morphine sulfate to the buffering agent from about 0.4 to about 1.3 and is in an amount sufficient to provide a pH of about 5 to the formulation; (d) a chelating agent; (e) a complement to a chelating agent; and (f) water.

In some embodiments, the formulation provided herein is stable at 80° C. for at least 14 days. In some embodiments, the formulation provided herein is stable at 40° C./75% RH for at least three months. In some embodiments, the formulation provided herein is stable at 25° C./60% RH for at least 12 months.

In some embodiments, the formulation provided herein is stored in a glass or plastic container which is stored in a secondary container having reduced permeability to oxygen and further comprising an oxygen scavenger. In certain instances, the formulation provided herein is stable at 40° C./75% RH for at least six months. In certain instances, the formulation provided herein is stable at 25° C./60% RH for at least 24 months.

Also provided herein are injectable formulations comprising per mL: (a) from about 2 mg to about 10 mg of morphine sulfate or a hydrate thereof; (b) sodium chloride; (c) a buffering system comprised of a buffering agent in an amount which provides a molar ratio of morphine sulfate to the buffering agent from about 0.4 to about 1.3 and is in an amount sufficient to provide a pH of about 5 to the formulation and a conjugate base to the buffering agent; (d) disodium edetate or a hydrate thereof; (e) calcium chloride or a hydrate thereof; and (f) water for injection.

In certain embodiments, the formulation comprises per mL: (a) from about 4 mg and 10 mg of morphine sulfate or a hydrate thereof; (b) sodium chloride; (c) a buffering agent in an amount which provides a molar ratio of morphine sulfate to the buffering agent from about 0.4 to 0.8 and is in an amount sufficient to provide a pH of about 5 to the formulation; (d) disodium edetate or a hydrate thereof; (e) calcium chloride or a hydrate thereof; and (f) water for injection.

In one embodiment of the formulation, the buffering agent is also an anti-oxidative agent. In another embodiment of the formulation, the buffering agent forms a buffer comprised of citric acid monohydrate and sodium citrate dihydrate.

In another embodiment, the formulation is stable at 80° C. for at least 14 days. In some embodiments, the formulation provided herein is stable at 40° C./75% RH for at least three months. In some embodiments, the formulation provided herein is stable at 25° C./60% RH for at least 12 months.

In another aspect, provided herein is a pharmaceutical formulation, e.g., an injectable pharmaceutical formulation, comprising per mL: (a) from about 2 mg to about 10 mg of morphine sulfate pentahydrate; (b) from about 7 mg to about 9 mg of sodium chloride; (c) from about 2 mg to about 4 mg of sodium citrate dehydrate; (d) from about 0.7 to about 1.2 mg of citric acid monohydrate; (e) from about 0.1 to about 0.15 mg of disodium edetate dihydrate; (f) from about 0.04 to about 0.06 mg calcium chloride dihydrate; and (g) water for injection.

In one embodiment, the formulation comprises per mL (a) about 2 mg morphine sulfate pentahydrate; (b) about 8.4 mg of sodium chloride; (c) about 2.3 mg of sodium citrate dehydrate; (d) about 0.74 mg of citric acid monohydrate; (e) about 0.111 mg of disodium edetate dihydrate; (f) about 0.053 mg calcium chloride dihydrate; and (g) water for injection.

In another embodiment, the formulation comprises per mL (a) about 4 mg morphine sulfate pentahydrate; (b) about 8.4 mg of sodium chloride; (c) about 2.3 mg of sodium citrate dehydrate; (d) about 0.74 mg of citric acid monohydrate; (e) about 0.111 mg of disodium edetate dihydrate; (f) about 0.053 mg calcium chloride dihydrate; and (g) water for injection.

In another embodiment, the formulation comprises per mL (a) about 5 mg morphine sulfate pentahydrate; (b) about 7.5 mg of sodium chloride; (c) about 3.45 mg of sodium citrate dehydrate; (d) about 1.11 mg of citric acid monohydrate; (e) about 0.111 mg of disodium edetate dihydrate; (f) about 0.053 mg calcium chloride dihydrate; and (g) water for injection.

In another embodiment, the formulation comprises per mL (a) about 8 mg morphine sulfate pentahydrate; (b) about 7.5 mg of sodium chloride; (c) about 3.45 mg of sodium citrate dehydrate; (d) about 1.11 mg of citric acid monohydrate; (e) about 0.111 mg of disodium edetate dihydrate; (f) about 0.053 mg calcium chloride dihydrate; and (g) water for injection.

In another embodiment, the formulation comprises per mL (a) about 10 mg morphine sulfate pentahydrate; (b) about 7.5 mg of sodium chloride; (c) about 3.45 mg of sodium citrate dehydrate; (d) about 1.11 mg of citric acid monohydrate; (e) about 0.111 mg of disodium edetate dihydrate; (f) about 0.053 mg calcium chloride dihydrate; and (g) water for injection.

In various embodiments, the formulation is stored in a glass or plastic container. In various other embodiments, the glass or plastic container is a prefilled syringe or a vial. In various other embodiments, the formulation is stored in a glass container which is stored in a secondary container having reduced permeability to oxygen and further comprising an oxygen scavenger. In certain instances, the formulation provided herein is stable at 40° C./75% RH for at least six months. In certain instances, the formulation provided herein is stable at 25° C./60% RH for at least 24 months.

In another aspect, provided herein is a method of reducing pain in a subject, comprising: administering to the subject a morphine pharmaceutical formulation, e.g., an injectable pharmaceutical formulation comprising per mL (a) from about 2 mg to about 10 mg of morphine sulfate or a hydrate thereof; (b) sodium chloride; (c) a buffering agent in an amount which provides a molar ratio of morphine sulfate to the buffering agent from about 0.4 to about 1.3 and is in an amount sufficient to provide a pH of about 5 to the formulation; (d) disodium edetate dihydrate; (e) calcium chloride dihydrate; and (f) water.

In another aspect, provided herein is a method of reducing adverse effects of a injectable morphine pharmaceutical formulation comprising disodium edetate dihydrate, the method comprising the addition of calcium chloride dihydrate to the injectable morphine pharmaceutical formulation wherein the formulation comprises per mL: (a) from about 2 mg to about 10 mg of morphine sulfate or a hydrate thereof; (b) sodium chloride; (c) a buffering agent in an amount which provides a molar ratio of morphine sulfate to the buffering agent from about 0.4 to about 1.3 and is in an amount sufficient to provide a pH of about 5 to the formulation; (d) disodium edetate dihydrate; (e) calcium chloride dihydrate; and (f) water.

In another aspect, provided herein is a kit comprising (a) a pre-filled syringe comprising a morphine formulation described herein; and (b) a secondary container having reduced permeability to oxygen and further comprising an oxygen scavenger.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings:

DETAILED DESCRIPTION OF THE INVENTION

Morphine Formulations for Injectable Administration

Figure 1:
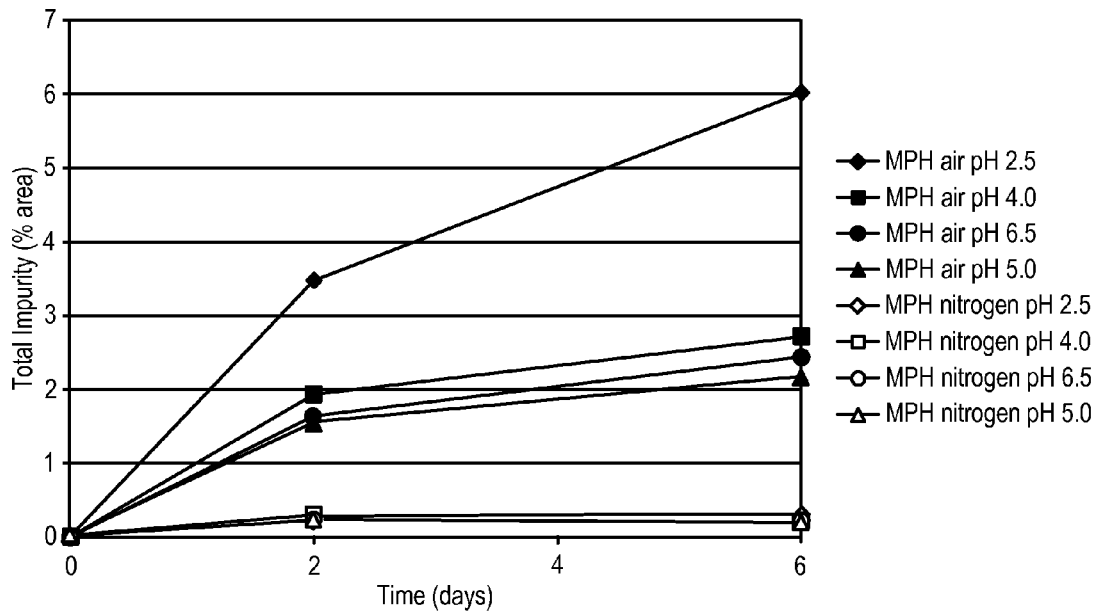
FIG. 1: Total impurities results by UPLC for 10 mg/mL morphine sulfate solution having pH 2.5, 4.0, 5.0 or 6.5 prepared under inert (nitrogen) or air conditions at storage condition at 80° C. for 6 days.

Provided herein are stable morphine formulations for injectable administration. These morphine formulations described herein are useful for the treatment and management of pain as well as anesthesia. The compositions are advantageous over conventional formulations of morphine ranging from increased stability, reduction of side effects and complementation to certain types of packaging.

The injectable morphine formulations described herein are stable over time (at least 2 years) when stored in a glass or plastic container. A feature of the formulations provided herein is that, under suitable storage, the level of total impurities is low (e.g., total impurities no more than 1.5% w/w of the Morphine sulfate assay, or total impurities no more than 0.5% w/w of the Morphine sulfate assay, over the period of shelf life). In specific embodiments, the pseudomorphine level, which is the main degradation product due to oxidation, is maintained under 0.2% all along the shelf life (i.e., no more than 0.2% w/w of the Morphine sulfate quantity).

As used herein, "morphine" refers to the base opioid alkaloid having the structure:

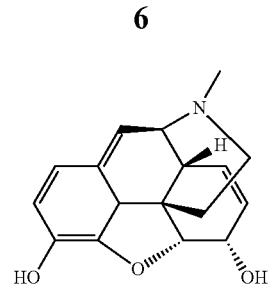

(5α,6α)-7,8-didehydro-4,5-epoxy-17-methylmorphi-nan-3,6-diol $C_{17}H_{19}NO_3$ or its salts, hydrates, solvates, derivatives or polymorphs thereof.

Suitable morphine forms for the formulations described herein include the free base, the organic and inorganic salts, isomers, isomer salts, solvates, polymorphs, complexes etc. Morphine is traditionally isolated and prepared from the opium poppy (*Papaver somniferum*). U.S. Pat. Nos. 1,048,712; 2,715,627; and 6,054,584 disclose exemplary methods for the isolation and preparation of morphine.

Anhydrous morphine or various morphine salts or hydrates are contemplated for use in the formulations provided herein, for example, morphine hydrochloride, morphine sulfate, morphine tartrate, morphine citrate, morphine methobromide, morphine hydrobromide, morphine hydroiodide, morphine lactate, morphine bitartrate, morphine tannate, morphine phosphate, morphine ascorbate and morphine acetate. In certain embodiments, the morphine, or a salt thereof, or a hydrate thereof used herein, is selected from morphine sulfate pentahydrate or morphine hydrochloride. In some embodiments, the morphine, or a salt thereof, or a hydrate thereof used herein is morphine hydrochloride. In other embodiments, the morphine, or a salt thereof, or a hydrate thereof used herein is morphine sulfate pentahydrate. Morphine sulfate pentahydrate has the following structural formula:

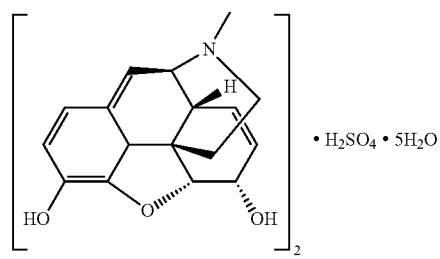

(5α,6α)-7,8-didehydro-4,5-epoxy-17-methylmorphi-nan-3,6-diol sulfate pentahydrate $(C_{17}H_{19}NO_3)_2 \cdot H_2SO_4 \cdot 5H_2O$ In some embodiments, morphine is present in a concentration of about 1 mg/mL to about 15 mg/mL of the morphine formulation. In some other embodiments, morphine is present in a concentration about 1 mg/mL, about 2 mg/mL, about 3 mg/mL, about 4 mg/mL, about 5 mg/mL, about 6 mg/mL, about 7 mg/mL, about 8 mg/mL, about 9 mg/mL, about 10 mg/mL, about 11 mg/mL, about 12 mg/mL, about 13 mg/mL, about 14 mg/mL or about 15 mg/mL of the morphine formulation. In certain embodiments, morphine is present in a concentration of about 2 mg/mL of the morphine formulation. In certain embodiments, morphine is present in a concentration of about 1 mg/mL of the morphine formulation. In certain embodiments, morphine is present in a concentration of about 4 mg/mL of the morphine formulation. In certain embodiments, morphine is present in a concentration of about 5 mg/mL of the morphine formulation. In certain embodiments, morphine is present in a concentration of about 8 mg/mL of the morphine formulation. In certain embodiments, morphine is present in a concentration of about 10 mg/mL of the morphine formulation. In certain embodiments, morphine is present in a concentration of about 15 mg/mL of the morphine formulation.

To provide the particular features described above, in one aspect, the morphine formulations herein comprise the following components or excipients: an isotonic agent, a buffering system, a chelating agent, and a complement to the chelating agent. These components impart improved stability and reduced degradation of morphine as compared to known marketed morphine products (see Example 7).

pH of the Morphine Formulations

Typical marketed injectable formulations of morphine vary in pH from about 2.5 to 6.5. Thus, in certain embodiments, morphine formulations described herein are contemplated to have a pH from about 2.5 to 6.5. However surprisingly, as shown in Example 1, maintaining the pH of morphine formulations close to 5 provides increased stability of morphine and enhances shelf life. Specifically, the morphine formulation at pH 5.0 showed lower total impurities during storage than other pH values. Accordingly, in some embodiments, provided herein are morphine injectable formulations having a pH of from about 4.5 to about 5.5, or from about 4.7 to about 5.2, or about 5. In certain embodiments, the morphine formulations described herein have a pH of about 5.0. In alternative embodiments, the morphine formulations described herein have a pH of about 4.0 which, according to Example 1, shows better stability than at other pH except for pH 5.0. The pH of the morphine formulations described herein are, in some embodiments, obtained via a buffer system in the formulation. In other embodiments, the desired pH is obtained by adjustment of the formulation with adjustment with an acid and base (e.g., HCl or $H_2SO_4$ and NaOH).

Isotonic Agents

Isotonic agents, also known as tonicity or tonicity-adjusting agents, increase isotonic compatibility with physiological environments with the injected morphine formulation. In some embodiments, the addition of an isotonic agent(s) provides an osmolality that is similar to or equal to blood osmolality. In other embodiments, the addition of an isotonic agent(s) provides an osmolality of about 280 to about 310 mOsm/Kg. Isotonic agents include, but are not limited to, electrolytes and saccharides (e.g., dextrose, lactose, mannitol, glucose, dextran, ammonium chloride, sodium chloride, calcium chloride, potassium chloride, sodium bicarbonate, sodium lactate, Ringer's solution, Lactated Ringer's solution, Normosol R, saline, Hartmann's solution, and mixtures and combinations thereof). In some embodiment, the isotonic agent is a Ringer's solution. In other embodiments, an isotonic agent is selected from mannitol, sodium chloride, glycerine, sodium lactate, potassium chloride, and calcium chloride. In further embodiments, the isotonic agent is sodium chloride. In certain instances, the sodium chloride is present at a concentration from about 5 to about 9 mg/mL in the morphine formulation. In certain instances, the sodium chloride is present at a concentration from about 7 to about 9 mg/mL in the morphine formulation. In other instances, the sodium chloride is present at a concentration at about 7.5 mg/mL in the morphine formulation. In yet other instances, the sodium chloride is present at a concentration at about 8.4 mg/mL in the morphine formulation. Concentrations of additional or other isotonic agents are obtained by determining the osmolality brought about by the morphine and other excipients in the formulation and calculating the concentration needed by the isotonic agent to provide an osmolality that is similar to or equal to blood osmolality and/or an osmolality of about 280 to about 310 mOsm/Kg.

Buffering System

The buffering system in the morphine formulations described herein function to keep the pH constant throughout the formulations' shelf life as well as providing anti-oxidant properties to prevent degradation. A feature of the buffer system, not present in existing morphine formulations, is that the buffering agent concentration is connected to the concentration of the active substance, morphine. Otherwise, an increase in the buffer concentration may cause an increase in pain perceived by the subject during and/or after injection of the morphine formulation. Hence, in some embodiments, the molar ratio of morphine to the buffering agent from about 0.4 to about 1.3 for a range of morphine concentrations between about 10 mg/mL and about 2 mg/mL. In other embodiments, molar ratio of morphine to the buffering agent from about 0.4 to about 0.8 for a range of morphine concentrations between about 10 mg/mL and about 4 mg/mL. The buffer ratios ensure the correct pH properties and the stability of the solution within the formulation's shelf life.

The buffering system comprises two components: a di-carboxylic or tri-carboxylic acid as a buffering agent and its conjugate base. Acids with more than one carboxylic acid group can act as chelating moieties for multivalent cations. Suitable acids include, but are not limited to, citric acid, iso citric acid, aconitic acid, trimesic acid, propane-1,2,3-tricarboxylic acid, fumaric acid, oxalic acid, maleic acid, malonic acid, glutaric acid, succinic acid or tartaric acid. In some embodiments, the morphine formulations described herein comprise a di-carboxylic or tri-carboxylic acid and its conjugate base. In other embodiments, the morphine formulations described herein comprise a buffering agent selected from citric acid, iso citric acid, aconitic acid, trimesic acid, propane-1,2,3-tricarboxylic acid, fumaric acid, oxalic acid, maleic acid, succinic acid or tartaric acid. In further embodiments, the morphine formulations described herein comprise citric acid. In yet further embodiments, the buffering system of the morphine formulations described herein comprises citric acid and sodium citrate in their anhydrous or hydrates forms. In certain instances, the morphine formulations described herein comprise citric acid monohydrate and sodium citrate dihydrate.

The two components of the buffer system can be varied to produce a desired pH. For example, citric acid can be increased while sodium citrate is decreased to lower the pH and conversely, citric acid can be decreased while sodium citrate is increased to raise the desired pH. Thus, by adjusting the concentrations of both components, pH values from 2.5 to 6.5 can be obtained. For the morphine formulations described herein, in some embodiments, the buffer system is in an amount sufficient to provide a pH of from about 2.5 to about 6.5 to the formulation. In other embodiments, the buffer system is in an amount sufficient to provide a pH of about 5.0. Exemplary buffer concentrations are described in more detail in Example 4.

Chelating Agents

Chelating agents, or complexing agents or sequestering agents complex or chelate metal ions and are useful in pharmaceutical formulations by complexing to metal ions such as $Zn^{2+}$, $Cu^{2+}$, $Mg^{2+}$, etc. that are present in containers. The presence of such metal ions can initiate reactions such as oxidation reactions that would indirectly lead to the degradation of the active drug substance. Exemplary chelating agents are EDTA (ethylenediaminetetraacetic acid or edetic acid) and EGTA (ethylene glycol tetraacetic acid) and their salts and hydrates thereof. Other chelating agents include, but are not limited to ethylenediamine, DPTA (pentetic or diethylene triamine pentaacetic acid), HEDTA (N-(hydroxyethyl)ethylenediaminetriacetic acid), NTA (aminotriacetic acid), DMPS (2,3-dimercapto-1-propanesulfonic acid), DMSA (dimercaptosuccinic acid), BAL (dimercaprol), BAPTA (1,2-bis(o-aminophenoxy)ethane-N,N,N',N'-tetraacetic acid), and their salts and hydrates thereof, porphyrins and the like. In some embodiments, the chelating agent is anhydrous EDTA or its salt or hydrated form. In some instances, the EDTA is disodium EDTA, calcium disodium EDTA, trisodium EDTA, tetrasodium EDTA, dipotassium EDTA, tripotassium EDTA, or the like. In certain instances, the EDTA is disodium EDTA. In some instances, the EDTA is present at a concentration at about 0.1 mg/mL in the morphine formulation. In some instances, the EDTA is present at a concentration at about 0.111 mg/mL in the morphine formulation. In other embodiments, the chelating agent is anhydrous EGTA or its salt or hydrated form. In further embodiments, the chelating agent is an EDTA/EGTA combination.

Complement to Chelating Agent

In addition to chelating metal ions that are present in pharmaceutical formulation containers, chelating agents can also chelate important ions in the body and interfere with physiological processes. For example, EDTA chelates serum $Ca^{2+}$ which can impair the blood coagulation pathway, calcium metabolism, signal transduction and, in certain amounts, can cause hypocalcaemia. To overcome the detrimental effects of chelating agents in the morphine formulations described herein, a complement to chelating agent is added, in some embodiments. Complements to chelating agent are certain agents which prevent chelation of endogenous metal ions such as calcium. In a non-limiting example, calcium chloride interacts with EDTA and prevents chelation of $Ca^{2+}$ from the blood. Because [EDTA-$Ca^{2+}$] have less stability than [EDTA-$Fe^{3+}$] (pKd [EDTA-$Ca^{2+}$]=10.7; pKd [EDTA-$Fe^{3+}$]=14.3) or any other heavy metals, EDTA preferentially chelates other metal ions when they are present and displaces calcium. In some embodiments, the chelating agent complement is a calcium salt. In some embodiments, the chelating agent complement is calcium chloride or a hydrate thereof. In other embodiments, the chelating agent complement is calcium gluconate or a hydrate thereof. In further embodiments, the chelating agent complement is calcium chloride dihydrate. In some instances, the calcium chloride is present at a concentration at about 0.05 mg/mL in the morphine formulation. In other instances, the calcium chloride is present at a concentration at about 0.053 mg/mL in the morphine formulation.

Vehicles

Liquid vehicles for the morphine formulations described herein are selected for suitability for injection as well as other qualities such as clarity, toxicity, viscosity, compatibility with excipients, chemical inertness, lack of color and economy. In the embodiments of the morphine formulations described herein, water for injection (e.g., USP grade) is, in certain instances, used as a vehicle for the formulation. In other instances, the vehicle for the morphine formulations described herein include solvents miscible with water. Such solvents include, but are not limited to, ethyl alcohol, propylene glycol, glycerin, polyethylene glycol, and polypropylene glycol. Additional known solvents that have compatibility with the excipients and morphine are contemplated within the scope of embodiments.

Additional Excipients

It is contemplated with the scope of the morphine formulations described herein to optionally comprise additional excipients including, but not limited to, preservatives and viscosity agents. Although the morphine formulations described herein are preservative-free, the addition of preservatives may further prevent degradation of the active ingredient, further prevent growth of microbials and/or further increase storage-life of the formulation. Non-limiting examples of preservatives include benzyl alcohol, phenol, benzoic acid, erythorbic acid, fumaric acid, malic acid, propyl gallate, BHA, BHT, parabens (methyl-, ethyl-, butyl-), cresol, vanillin, chlorobutanol, benzoates, sulfites, sorbic acid and sorbates. Viscosity agents refer to excipients that increase compatibility and/or iso-viscosity with the physiological site of injection. For example, the morphine formulations described herein can be formulated with a viscosity agent to provide compatible viscosity with that of blood. Exemplary viscosity agents include hyaluronic acid, sodium hyaluronate, polyethylene glycol, chitosan, fucans, copolymers of polysaccharides with degradable polymers, gelatin, starch, cellulose, cellulose derivatives, glycerol and the like. In some embodiments, the morphine formulations described herein optionally comprise a preservative. In other embodiments, the morphine formulations described herein optionally comprise viscosity agent.

It is further contemplated that the morphine formulations described herein, in some embodiments, are suitable for oral administration. Morphine formulations for oral administration contain, in some embodiments, additional excipients to enhance the palatability of the formulation. These include but are not limited to sweetening agents or sweeteners, flavorants, bitter taste masking agents, and colorants.

Sweeteners or sweetening agents include any compounds that provide a sweet taste. This includes natural and synthetic sugars, natural and artificial sweeteners, natural extracts and any material that initiates a sweet sensation in a subject. In some embodiments, the morphine formulations described herein described herein comprise a sweetener. Sugars illustratively include glucose, fructose, sucrose, xylitol, tagatose, sucralose, maltitol, isomaltulose, Isomalt™ (hydrogenated isomaltulose), lactitol, sorbitol, mannitol, erythritol, trehalose, maltodextrin, polydextrose, and the like. Other sweeteners illustratively include glycerin, inulin, erythritol, maltol, acesulfame and salts thereof, e.g., acesulfame potassium, alitame, aspartame, neotame, sodium cyclamate, saccharin and salts thereof, e.g., saccharin sodium or saccharin calcium, neohesperidin dihydrochalcone, stevioside, thaumatin, and the like. Sweeteners can be used in the form of crude or refined products such as hydrogenated starch hydrolysates, maltitol syrup, high fructose corn syrup, etc., and as branded products, e.g., Sweet Am™ liquid (Product Code 918.003—propylene glycol, ethyl alcohol, and proprietary artificial flavor combination, Flavors of North America) and SweetAm™ powder (Product Code 918.005—maltodextrin, sorbitol, and fructose combination and Product Code 918.010—water, propylene glycol, sorbitol, fructose, and proprietary natural and artificial flavor combination, Flavors of North America), ProSweet™ (1-10% proprietary plant/vegetable extract and 90-99% dextrose combination, Viriginia Dare), Maltisweet™ (maltitol solution, Ingredion) and Sorbo™ (sorbitol and sorbitol/xylitol solution, SPI Polyols), Invertose™ (high fructose corn syrup, Ingredion) and Ora-Sweet® sugar-free flavored syrup (Paddock Laboratories, Inc.). Sweeteners can be used singly or in combinations of two or more. Suitable concentrations of different sweeteners can be selected based on published information, manufacturers' data sheets and by routine testing.

In another embodiment, the morphine formulations described herein for oral administration comprise a flavoring agent or flavorant to enhance the taste or aroma of the composition for oral administration. Suitable natural or synthetic flavoring agents can be selected from standard reference books, for example Fenaroli's Handbook of Flavor Ingredients, 3rd edition (1995). Non-limiting examples of suitable natural flavors, some of which can readily be simulated with synthetic agents or combinations thereof, include almond, anise, apple, apricot, bergamot, blackberry, blackcurrant, blueberry, cacao, caramel, cherry, cinnamon, clove, coffee, coriander, cranberry, cumin, dill, eucalyptus, fennel, fig, ginger, grape, grapefruit, guava, hop, lemon, licorice, lime, malt, mandarin, molasses, nutmeg, orange, peach, pear, peppermint, pineapple, raspberry, rose, spearmint, strawberry, tangerine, tea, vanilla, wintergreen, etc. Also useful, particularly where the formulation is intended primarily for pediatric use, is tutti-frutti or bubblegum flavor, a compounded flavoring agent based on fruit flavors. Presently preferred flavoring agents include anise, cinnamon, cacao, orange, peppermint, cherry (in particular wild cherry), grape, bubblegum and vanilla. In some embodiments, the morphine formulations described herein for oral administration comprise a wild cherry flavoring agent. Flavoring agents can be used singly or in combinations of two or more.

Because morphine is known to have a bitter taste, in some embodiments, the morphine formulations described herein for oral administration comprise a bitter taste inhibiting or masking agent. Bitter taste inhibiting or masking agents include, but are not limited to, a sweetener or flavorant as described above, alkali metal salts such as sodium chloride, sodium bicarbonate, potassium bicarbonate, magnesium bicarbonate, sodium carbonate, potassium carbonate, magnesium carbonate, sodium citrate, sodium tartrate, sodium biphosphate, sodium phosphate, potassium phosphate or magnesium trisilicate and the like.

In further embodiments, the morphine formulations described herein for oral administration comprise a coloring agent for identity and/or aesthetic purposes of the resultant liquid form. Suitable coloring agents illustratively include FD&C Red No. 3, FD&C Red No. 20, FD&C Red No. 40, FD&C Yellow No. 6, FD&C Blue No. 2, D&C Green No. 5, D&C Orange No. 5, caramel, ferric oxide and mixtures thereof.

Preparation of Morphine Formulations

Preparation of the morphine formulations described herein includes any known pharmaceutical method. In one embodiment, the morphine formulations described are prepared by the addition of the drug and the excipients into a formulation tank containing a liquid vehicle. The tank agitates or mixes the liquid vehicle to promote the dissolving of the various components into the liquid vehicle. The drug and each excipient can be added to the tank sequentially after the prior ingredient has dissolved. After liquid formulation is mixed, it can be further filtered to remove particulates and reduce bioburden, and provide sterility by employing one or more additional filters (e.g., 0.22 μm). An exemplary preparation is described in Example 4.

In an alternative embodiment, the morphine formulations described are prepared first by a direct blend method of the drug and various excipients as a dry powder and then subsequently reconstituted in a liquid vehicle. For example, morphine is blended along with any other excipients in a dry mixer or blender. In certain instances, the powders are passed through a mesh screen prior to and/or after mixing. The dry blend is facilitated by conventional large-scale mixing equipment such as rotating-shell mixers (e.g., drum-type, cubical shaped, double-cone and twin-shell blender), fixed-shell (ribbon) mixers, sigma-blade and planetary paddle mixers, vertical impeller mixers and motionless mixers. The mixing is performed to blend uniformity of a powder mixture of the morphine formulations described herein. In these embodiments, mixing methods can include all components together or incorporate certain components together first with other components subsequently added.

In the preparation embodiments of the morphine formulations described herein, the preparation is, in some instances, in an environment containing an inert gas. The use of an inert gas (e.g., nitrogen, argon, $CO_2$, helium and the like) limit the morphine and the excipients to oxygen exposure. Liquid vehicles and other solutions are also sparged or bubbled by the inert gas to remove oxygen in the liquid. The solutions are then filled and sealed into primary containers and, in some embodiments, secondary packaging under inert gas.

Stability of Morphine Formulations

The morphine formulations described herein are stable in various storage conditions including ambient and accelerated conditions. Stability as used herein refers to a formulation meeting all stability criteria along its particular shelf life, as defined in the USP or equivalent monograph of the drug product (for the assay of the drug substance in particular) and the current stability criteria of the ICH Q3B guidance for impurities. All critical quality attributes need to stay in their acceptance range throughout the formulation's shelf life. For a morphine formulation to be stable, assay of the drug substance, i.e., morphine, is in the [90.0%-110.0%] range as per USP and per ICH Q3B guidelines, all known, i.e., identified, degradation products, such as pseudomorphine, hydroxymorphine, norphine-N-oxide, and the like, as well as unknown degradation products need to be no more than (NMT) 0.2%. Stability of the morphine formulations described herein is assessed by HPLC, UPLC or any other known analytical method.

In some embodiments, the morphine formulations described herein are stable in ambient conditions (e.g., 25° C./60% RH) for at least 6 months, at least 8 months, at least 10 months, at least 12 months, or at least 24 months. In certain instances, the morphine formulations described herein are stable in ambient conditions for at least 12 months. In certain instances, the morphine formulations described herein are stable in ambient conditions for at least 24 months. In other embodiments, the morphine formulations described herein are stable in intermediate conditions (e.g., 30° C./65% RH) for at least 4 months, at least 5 months, at least 6 months, at least 9 months, or at least 12 months. In certain instances, the morphine formulations described herein are stable in intermediate conditions for at least 6 months. In certain instances, the morphine formulations described herein are stable in intermediate conditions for at least 12 months. In further embodiments, the morphine formulations described herein are stable in accelerated conditions (e.g., 40° C./75% RH) for at least 1 month, at least 2 months, at least 3 months, at least 4 months, at least 5 months, or at least 6 months. In certain instances, the morphine formulations described herein are stable in accelerated conditions for at least 3 months. In certain instances, the morphine formulations described herein are stable in accelerated conditions for at least 6 months. In yet further embodiments, the morphine formulations described herein are stable in 80° C. test conditions for at least 10 days, at least 12 days, or at least 14 days. In certain instances, the morphine formulations described herein are stable in 80° C. test conditions for at least 14 days. In the stability embodiments of this paragraph, the morphine formulations are stored without any oxygen barrier packaging, i.e., the morphine formulations are manufactured and filled under nitrogen in oxygen permeable containers.

When the morphine formulations described herein are stored in oxygen barrier packaging, the stability is improved. In some embodiments where morphine formulations described herein are stored in oxygen barrier packaging, the morphine formulations are stable in ambient conditions (e.g., 25° C./60% RH) for at least 12 months, at least 15 months, at least 18 months, or at least 24 months. In certain instances, the morphine formulations stored in oxygen barrier packaging are stable in ambient conditions for at least 24 months. In other embodiments where morphine formulations described herein are stored in oxygen barrier packaging, the morphine formulations are stable in intermediate conditions (e.g., 30° C./65% RH) for at least 6 months, at least 8 months, at least 10 months or at least 12 months. In certain instances, the morphine formulations stored in oxygen barrier packaging are stable in intermediate conditions for at least 12 months. In further embodiments where morphine formulations described herein are stored in oxygen barrier packaging, the morphine formulations are stable in accelerated conditions (e.g., 40° C./75% RH) for at least 4 months, at least 5 months, or at least 6 months. In certain instances, the morphine formulations stored in oxygen barrier packaging are stable in accelerated conditions for at least 6 months. In yet further embodiments where morphine formulations described herein are stored in oxygen barrier packaging, the morphine formulations are stable in 80° C. test conditions for at least 10 days, at least 12 days, or at least 14 days. In certain instances, the morphine formulations stored in oxygen barrier packaging are stable in 80° C. test conditions for at least 14 days.

In some embodiments, the morphine formulations described herein stored in ambient conditions (e.g., 25° C./60% RH) have a pseudomorphine impurity not more than or equal to about 0.2% for at least 6 months, at least 8 months, at least 10 months, or at least 12 months of storage. In certain instances, the morphine formulations described herein stored in ambient conditions have a pseudomorphine impurity not more than or equal to about 0.2% for at least 12 months of storage. In other embodiments, the morphine formulations described herein stored in intermediate conditions (e.g., 30° C./65% RH) have a pseudomorphine impurity not more than or equal to about 0.2% for at least 4 months, at least 5 months, or at least 6 months of storage. In certain instances, the morphine formulations described herein stored in intermediate conditions have a pseudomorphine impurity not more than or equal to about 0.2% for at least 6 months of storage. In further embodiments, the morphine formulations described herein stored in accelerated conditions (e.g., 40° C./75% RH) have a pseudomorphine impurity not more than or equal to about 0.2% for at least 1 month, at least 2 months, or at least 3 months of storage. In certain instances, the morphine formulations described herein stored in accelerated conditions have a pseudomorphine impurity not more than or equal to about 0.2% for at least 3 months of storage. In the stability embodiments of this paragraph, the morphine formulations are stored without any oxygen barrier packaging, i.e., the morphine formulations are manufactured and filled under nitrogen in oxygen permeable containers.

In some embodiments, the morphine formulations described herein in oxygen barrier packaging and stored in ambient conditions (e.g., 25° C./60% RH) have a pseudomorphine impurity not more than or equal to about 0.2% for at least 12 months, at least 15 months, at least 18 months, or at least 24 months of storage. In certain instances, the morphine formulations described herein in oxygen barrier packaging and stored in ambient conditions have a pseudomorphine impurity not more than or equal to about 0.2% for at least 24 months of storage. In certain instances, the morphine formulations described herein in oxygen barrier packaging and stored in ambient conditions have a pseudomorphine impurity not more than or equal to about 0.1% for at least 24 months of storage. In other embodiments, the morphine formulations described herein in oxygen barrier packaging and stored in intermediate conditions (e.g., 30° C./65% RH) have a pseudomorphine impurity not more than or equal to about 0.1% for at least 6 months, at least 8 months, at least 10 months or at least 12 months of storage. In certain instances, the morphine formulations described herein in oxygen barrier packaging and stored in intermediate conditions have a pseudomorphine impurity not more than or equal to about 0.1% for at least 12 months of storage. In further embodiments, the morphine formulations described herein in oxygen barrier packaging and stored in accelerated conditions (e.g., 40° C./75% RH) have a pseudomorphine impurity not more than or equal to about 0.1% for at least 4 months, at least 5 months, or at least 6 months of storage. In certain instances, the morphine formulations described herein in oxygen barrier packaging and stored in accelerated conditions have a pseudomorphine impurity not more than or equal to about 0.1% for at least 6 months of storage.

In some embodiments, the morphine formulations described herein stored in ambient conditions (e.g., 25° C./60% RH) have a total impurity not more than or equal to about 0.8%, not more than or equal to about 0.7%, or not more than or equal to about 0.6% for at least 6 months, at least 8 months, at least 10 months, or at least 12 months of storage. In certain instances, the morphine formulations described herein stored in ambient conditions have a total impurity not more than or equal to about 0.8% for at least 12 months of storage. In other embodiments, the morphine formulations described herein stored in intermediate conditions (e.g., 30° C./65% RH) have a total impurity not more than or equal to about 0.4% or not more than or equal to about 0.3% for at least 4 months, at least 5 months, or at least 6 months of storage. In certain instances, the morphine formulations described herein stored in intermediate conditions have a total impurity not more than or equal to about 0.4% for at least 6 months of storage. In further embodiments, the morphine formulations described herein stored in accelerated conditions (e.g., 40° C./75% RH) have a total impurity not more than or equal to about 0.5% or not more than or equal to about 0.4% for at least 1 month, at least 2 months, or at least 3 months of storage. In certain instances, the morphine formulations described herein stored in accelerated conditions have a total impurity not more than or equal to about 0.5% for at least 3 months of storage. In the stability embodiments of this paragraph, the morphine formulations are stored without any oxygen barrier packaging, i.e., the morphine formulations are manufactured and filled under nitrogen in oxygen permeable containers.

In some embodiments, the morphine formulations described herein in oxygen barrier packaging and stored in ambient conditions (e.g., 25° C./60% RH) have a total impurity not more than or equal to about 1.5%, not more than or equal to about 1.2%, or not more than or equal to about 1.0% for at least 12 months, at least 15 months, at least 18 months, or at least 24 months of storage. In certain instances, the morphine formulations described herein in oxygen barrier packaging and stored in ambient conditions have a total impurity not more than or equal to about 1.5% for at least 24 months of storage. In certain instances, the morphine formulations described herein in oxygen barrier packaging and stored in ambient conditions have a total impurity not more than or equal to about 1.0% for at least 24 months of storage. In other embodiments, the morphine formulations described herein in oxygen barrier packaging and stored in intermediate conditions (e.g., 30° C./65% RH) have a total impurity not more than or equal to about 0.5% or not more than or equal to about 0.4% for at least 6 months, at least 8 months, at least 10 months or at least 12 months of storage. In certain instances, the morphine formulations described herein in oxygen barrier packaging and stored in intermediate conditions have a total impurity not more than or equal to about 0.4% for at least 12 months of storage. In further embodiments, the morphine formulations described herein in oxygen barrier packaging and stored in accelerated conditions (e.g., 40° C./75% RH) have a total impurity not more than or equal to about 0.5%, not more than or equal to about 0.3% or not more than or equal to about 0.2% for at least 4 months, at least 5 months, or at least 6 months of storage. In certain instances, the morphine formulations described herein in oxygen barrier packaging and stored in accelerated conditions have a total impurity not more than or equal to about 0.5% for at least 6 months of storage.

Methods

Provided herein, in one aspect, are methods of treatment comprising administration of the morphine formulations described herein to a subject. In some embodiments, the morphine formulations described herein treat, manage or reduce pain in a subject. Pain as used herein includes both moderate to severe pain and gradations thereof as well as acute and chronic pain. Pain can be caused by a disease (e.g., cancer), injury, or medical procedure (e.g., surgery). Pain intensity can be measured by a subject's self reporting, observations on behavior or activity and/or physiological data. Self reporting on pain includes measurement via a pain scale. For example, a simple pain scale may include such values as 0=no pain; 1-3=mild pain that may interfere with daily activities; 4-6=moderate pain that interferes with daily activities; and 7-10=severe pain that disables daily activities.

In certain instances, the morphine formulations described herein treat, manage or reduce moderate to severe pain in a subject. In the morphine formulations described herein treat, manage or reduce moderate pain in a subject. In other instances, the morphine formulations described herein treat, manage or reduce severe pain in a subject. In further instances, the morphine formulations described herein treat, manage or reduce acute or chronic pain in a subject.

In further embodiments, the morphine formulations described herein induce anesthesia in a subject preparing for or undergoing surgery. In yet further embodiments, the morphine formulations described herein treat acute pulmonary edema.

In another aspect, the morphine formulations described herein reduce adverse effects of a injectable morphine pharmaceutical formulation comprising a chelating agent such as EDTA. In some embodiments morphine formulations described herein comprise a complement to the chelating agent (e.g., calcium chloride), the effects of the chelating agent are diminished or dampened. This is advantageous in that the morphine formulations described herein have reduced side effects of chelating agents including impairment of blood coagulation, calcium metabolism, calcium signal transduction. The morphine formulations described herein are also suitable for subjects that have hypocalcaemia. In some embodiments, the morphine formulations described herein are administered to subjects having hypocalcaemia.

Dosing and Administration

Administration of a morphine formulation described herein is at a dosage described herein or at other dose levels and compositions determined and contemplated by a medical practitioner. Factors that may affect the dose and administration of a morphine formulation described herein include: the total daily dose, potency and specific characteristics of the opioid the subject has previously taken; the subject's degree of opioid tolerance; the general condition and medical status of the subject; concurrent medications; type and severity of the subject's pain; and risk factors and prior history for abuse and addiction.

In some embodiments, the morphine formulations described herein are provided at a dose per administration from about 0.5 mg to about 15 mg, from about 1 mg to about 12 mg, or from about 2 to about 10 mg of morphine. In certain embodiments, the morphine formulations described herein are provided at a dose per administration of about 0.5 mg, about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg of morphine, or any amount between therein. In certain instances, the morphine formulations described herein are provided at a dose per administration of about 2 mg. In certain instances, the morphine formulations described herein are provided at a dose per administration of about 4 mg. In certain instances, the morphine formulations described herein are provided at a dose per administration of about 5 mg. In certain instances, the morphine formulations described herein are provided at a dose per administration of about 8 mg. In certain instances, the morphine formulations described herein are provided at a dose per administration of about 10 mg.

In other embodiments, the morphine formulations described herein are provided at a dose per administration from about 0.01 mg/kg to about 0.2 mg/kg morphine per body weight in a subject, from about 0.02 mg/kg to about 0.17 mg/kg morphine per body weight in a subject, or from about 0.03 mg/kg to about 0.14 mg/kg morphine per body weight in a subject.

In further embodiments, the morphine formulations described herein are provided at a dose sufficient to manage or relieve pain in a subject. In other embodiments, the morphine formulations described herein are provided at a dose sufficient to induce anesthesia in a subject. In yet other embodiments, the morphine formulations described herein are provided at a dose sufficient to treat or mange acute pulmonary edema in a subject.

The dosages of the morphine formulations described herein are administered, in some embodiments, once per day. In other embodiments, dosages are administered b.i.d., t.i.d., q.i.d., or the like or according to the judgment of the health practitioner. The dosages of the morphine formulations described herein can be administered intravenously or intramuscularly by injection. In some embodiments, the morphine formulations described herein are administered intravenously. In other embodiments, the morphine formulations described herein are administered intramuscularly.

Because prolonged administration of morphine has potential for addiction or overdose, the administration of the morphine formulations described herein may be temporarily suspended for a certain length of time (i.e., a "drug holiday"). In specific embodiments, the length of the drug holiday is, by way of example only, between 2 days and 6 months, including 2 days, 3 days, 4 days, 5 days, 6 days, 7 days, 10 days, 12 days, 15 days, 20 days, 28 days, 35 days, 50 days, 70 days, 100 days, 120 days, 150 days and 180 days. Alternatively, the morphine formulations described herein, in some embodiments, are rotated out as part of an opioid rotation program. In an opioid rotation, administration of the morphine formulations described herein is suspended and an equianalgesic dose of another opioid is administered in its place. See Fine P G, et al., *J Pain Symptom Manage.* 2009; 38(3):418-425. Other opioids contemplated for a rotation, include but are not limited to, hydromorphone, oxycodone, oxymorphone, fentanyl, tramadol, sufentanil and the like.

The morphine formulations described herein are suitable for parenteral or oral administration. Parenteral administration includes injections via intravenous, intramuscular, subcutaneous, intradermal, intraspinal, intra-articular, and the like. In some embodiments, the morphine formulations described herein are administered by injection. In certain instances, the injection is intravenous. In certain instances, the injection is intramuscular. In certain instances, the injection is subcutaneous. In other embodiments, the morphine formulations described herein are administered orally as an oral solution.

Further Combinations

The treatment, management or reduction of certain conditions (e.g., pain) in a subject with a morphine formulation described herein encompasses additional therapies and treatment regimens with other agents in some embodiments. Such additional therapies and treatment regimens can include another therapy, e.g., additional analgesics such as other opioids (e.g., "opioid rotation"). Alternatively, in other embodiments, additional therapies and treatment regimens include other agents such as a chemotherapy used to treat the underlying disease or condition or to reduce or prevent a side effect from the morphine formulation in the therapy.

Packing for Morphine Formulations

Primary Packaging

Various types of containers (i.e., primary packaging) are suitable for the containment of the morphine formulations described herein. Examples of such containers include, without limitation, vials, syringes, ampoules, bottles, cartridges, carpules and intravenous bags or pouches. In some embodiments, the morphine formulations described herein are packaged or filled in a container selected from a vial, syringe, ampoule, bottle, cartridge, carpule and a bag.

Vials for the containment of the morphine formulations described herein generally have open mouths which are normally closed with an elastomer closure through which a hollow needle may be passed and via which liquid may be introduced or removed from the vial. Vials are typically made of type I glass or may be made of plastic such as PET. Suitable elastomers for such closures include, for example, vulcanized elastomers and styrenic block copolymer thermoplastic elastomers, but also natural rubber, acrylate-butadiene rubber, cis-polybutadiene, chlroro or bromobutyl rubber, chlorinated polyethylene elastomers, polyalkylene oxide polymers, ethylene vinyl acetate, fluorosilicone rubbers, hexafluoropropylene-vinylidene fluoride-tetrafluoroethylene terpolymers, butyl rubbers, polyisobutene, synthetic polyisoprene rubber, silicone rubbers, styrene-butadiene rubbers, tetrafluoroethylene propylene copolymers, thermoplastic-copolyesters, thermo-plastic elastomers, or the like or a combination thereof.

Syringes generally comprise a cylindrical barrel, often made of glass but more recently have been made of plastic materials, for example, cyclic olefin polymers or acrylonitrile butadiene styrene (ABS), polycarbonate (PC), polyoxymethylene (POM), polystyrene (PS), polybutylene terephthalate (PBT), polypropylene (PP), polyethylene (PE), polyamide (PA), thermoplastic elastomer (TPE) and their combinations. The barrels of such syringes are operated with an elastomer plunger which can be urged along the barrel to eject liquid content via a nozzle. Suitable elastomers for such plungers may be based on the same thermoplastic elastomers as mentioned above for vial closures. Ampoules are a type of sealed glass vial which are generally opened by snapping off the neck or the top of the ampoule. Cartridges and carpules are specialized containers that are inserted into a drug delivery device (e.g. syringe or autoinjector). Finally, intravenous bags and pouches are typically used for infusion therapy or multiple dose administration. The bags and pouches are made from materials that have gas barrier properties.

For the more rigid containers, glass as provides various benefits. Glass is generally considered to not be permeable to moisture and gas permeation. An alternative group of materials, cyclic olefin polymers, polypropylene or polyethylene terephthalate are suitable for the containers as they typically have less breakage concerns as compared to glass and still exhibit good transparency. These materials include cyclic olefin copolymers such as Topas™ polymer (Topas Advanced Polymers GmbH) and cyclic olefin homopolymers such as Crystal Zenith™ polymer (Dalkyo).

As morphine has sensitivity to light, the primary packaging container should have light barrier properties. Exemplary glass or plastic containers for the morphine formulations described herein are amber or opaque to light. A primary packaging made of transparent materials may also be suitable provided it is placed in secondary or tertiary packaging materials that are opaque to light.

In one embodiment, the morphine formulations described herein are contained in a syringe primary packaging container. Exemplary syringes for use in the pharmaceutical packaging systems described herein include those described in U.S. Pat. Nos. 6,196,998; 6,200,627; 6,217,550; 6,743,216; 7,141,042; and 8,075,535; U.S. Pat. Appl. No. 2011/0130717; and U.S. application Ser. No. 13/622,391 each of which is incorporated by reference for their disclosure relating to syringe assembly.

Secondary Packaging

In some embodiments, the morphine formulations in a primary packaging container described herein benefit from the addition secondary packaging that envelops the primary packaging container. The secondary packaging provides additional barriers to elements that can degrade morphine such as light and oxygen. Some primary packaging containers may also be designed to permeable to oxygen and other gases. For example, syringes, cartridges and the like can have permeable parts (e.g., syringe tip cap and stoppers) to allow sterilization process with, for example, ethylene oxide. A primary packaging container may also be permeable because it is formed of permable materials, i.e., a plastic that is not impermeable to gases. Thus, a primary packaging container with a gas permeable component may cause the morphine formulations herein to degrade by allowing oxygen to permeate inside the container. As shown in Example 5, this degradation can lead to unacceptable levels.

Figure 11:
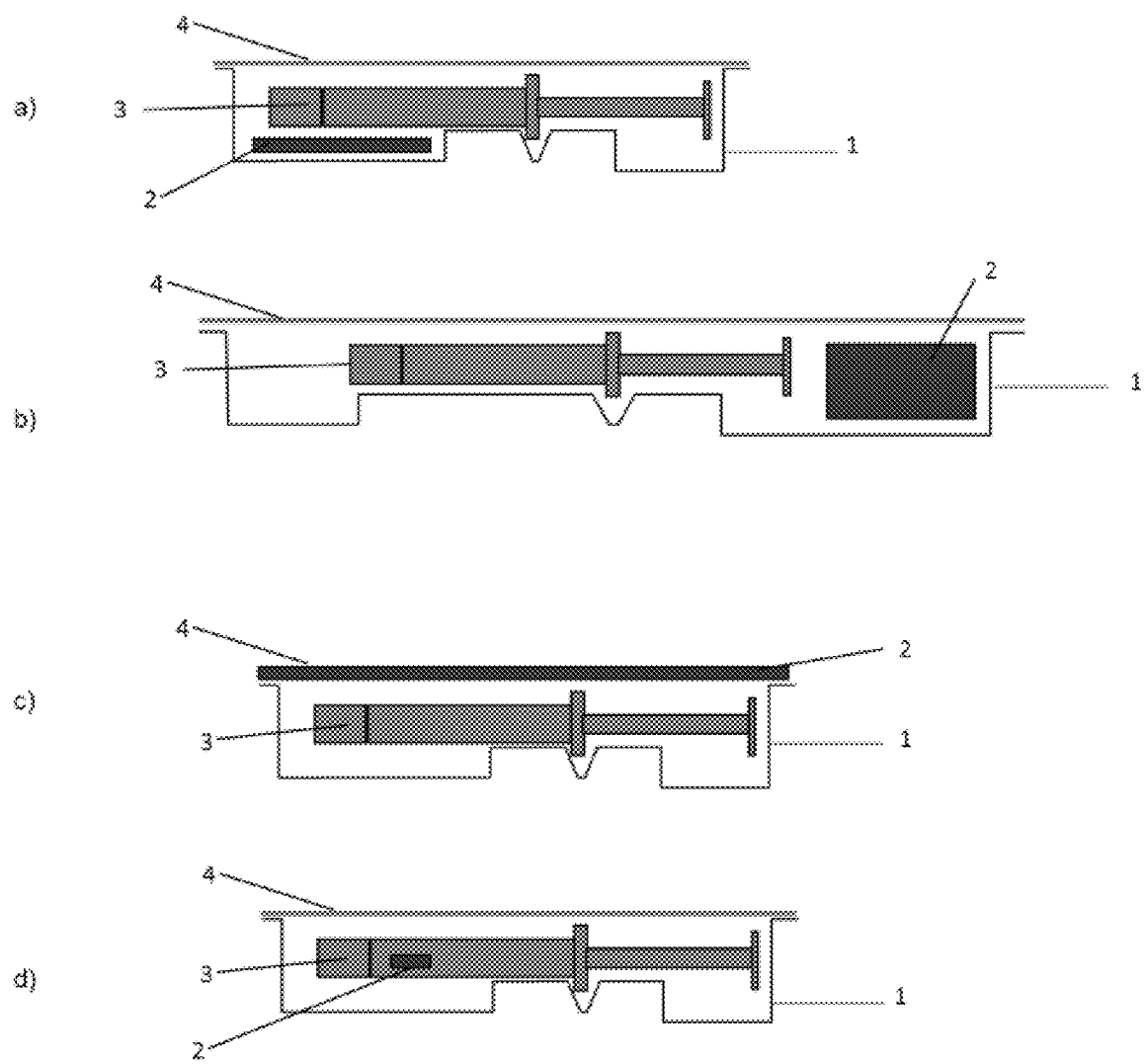
FIG. 11: Schematic of exemplary packaging system embodiments with oxygen absorber in a sachet (a), in the lid (b), in a canister (c) and positioned on the primary packaging (d).

It is therefore contemplated that the morphine formulations describe herein comprise a secondary packaging in addition to the primary packaging container. Secondary packaging includes any container that receives the primary packaging container (e.g., a box, bag, blister, canister, bottle and the like) and is sealed to prevent ingress of oxygen. The secondary packaging is made from material that has very low permeability to oxygen molecules (e.g., ethylene vinyl alcohol, aluminum, glass, polyamide and the like). In certain instances, the secondary packaging further comprises an oxygen absorber inside. The oxygen absorber functions to absorb any oxygen present in the secondary packaging. Suitable materials for oxygen absorbers include iron, low molecular weight organic compounds such as ascorbic acid and sodium ascorbate and polymeric materials incorporating a resin and a catalyst. Oxygen absorbers are contemplated to be in any size or shape including sachet, pouch, canister, lining, sticker, etc. as well as part of the secondary packaging or primary packaging container itself. Various secondary packaging and oxygen absorber configurations are depicted in FIG. 11. FIG. 1 illustrates different configurations of the secondary packaging and oxygen absorber embodiments with an oxygen absorber (2) as a sachet (FIG. 11a) placed inside the secondary packaging (1) and under the syringe primary packaging (3), in the lid 4 (FIG. 11b) of secondary packaging (1) and as a canister (FIG. 11c) placed next to the syringe primary packaging. Another embodiment where the oxygen absorber is positioned directly on the syringe primary packaging is also illustrated (FIG. 11d). An exemplary secondary packaging with an oxygen absorber is described in Example 6. In another embodiment, the morphine formulations describe herein in a syringe primary packaging container is placed inside a secondary packaging container.

Figure 12:
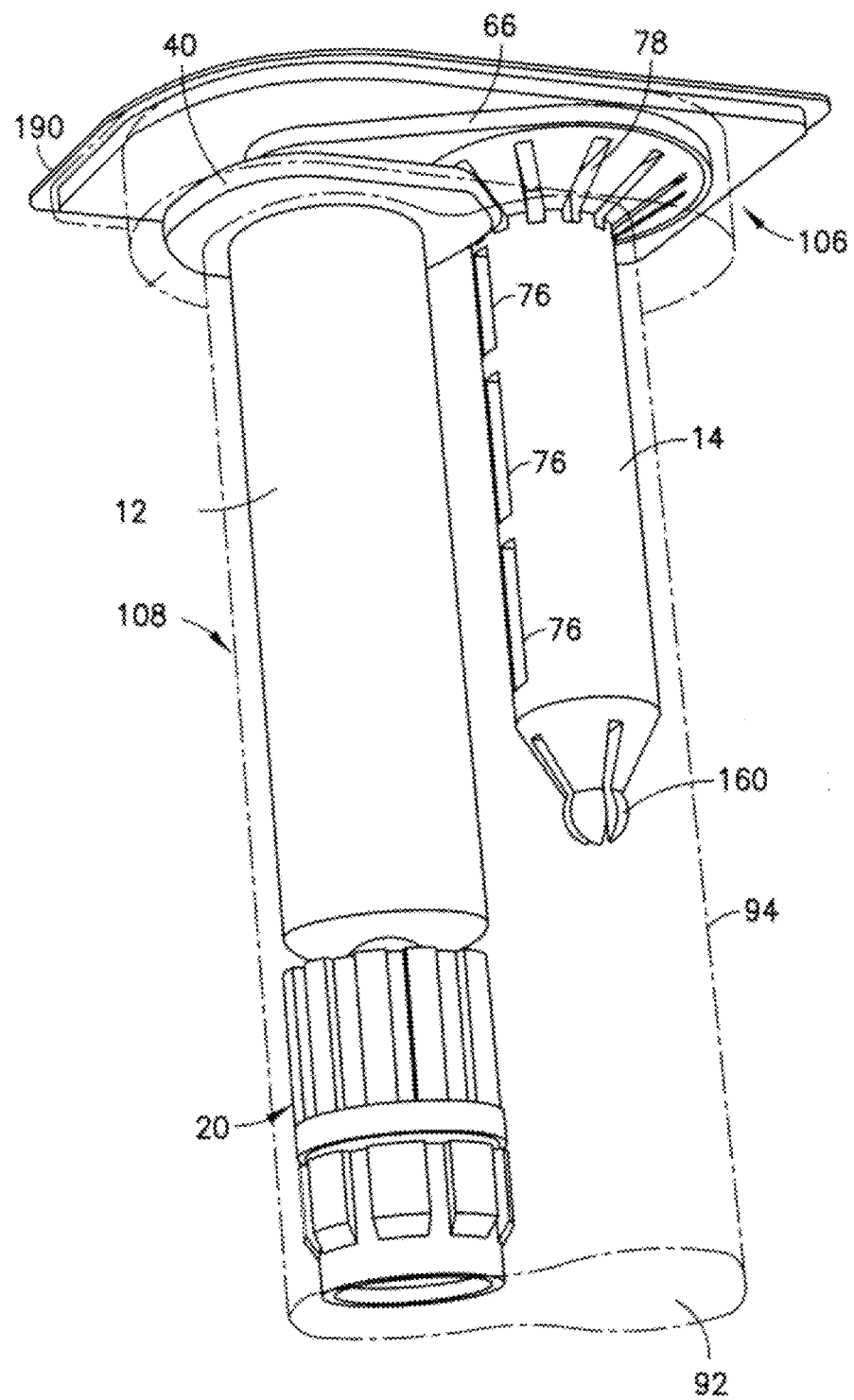
FIG. 12: Drawing of a exemplary syringe and secondary packaging embodiment where a secondary packaging includes a first compartment to receive a syringe barrel and second compartment to receive a plunger rod separate and detached from the syringe barrel.

In a further embodiment, a secondary packaging container suitable for the morphine formulations described herein is provided which includes a first compartment to receive a syringe barrel and second compartment to receive a plunger rod separate and detached from the syringe barrel. With the syringe barrel received in the first compartment and the plunger rod received within the second compartment, the sealing member of the plunger rod seals the syringe barrel and the plunger rod within the secondary packaging. This secondary packaging container configuration allows for reduced storage space of the syringe. In this manner, upon removal of the plunger rod and the syringe barrel from the secondary packaging, the plunger rod can quickly and easily be secured to the syringe barrel via a stopper for delivery of a morphine formulation described herein. An exemplary syringe and secondary packaging configuration is depicted in FIG. 12. FIG. 12 shows a syringe barrel (30) containing a morphine formulation described herein with a sealing cap (20) and a flange (40) for a user's fingers received in a first compartment portion (108) and a plunger rod (14) received in a second compartment portion (94) of a secondary packaging (92). The plunger rod (14) can comprise elastic fingers (160) which lock and secure to the syringe barrel (30), a flange (66) for usability, key slots (78) for securing the plunger rod in the second compartment of the secondary packaging and vents (76) to allow oxygen removal with an oxygen absorber (not shown). The secondary packaging with the syringe components is sealed with a sealing cover (190). It is envisioned that an oxygen absorber is in this configuration. Additional secondary packaging configurations for the morphine formulations described herein are found in U.S. Ser. No. 13/622,391, which is incorporated by reference for the relating to syringe and packaging assembly.

Kits and Articles of Manufacture

For the morphine formulations described herein, kits and articles of manufacture are also described. Such kits can comprise a secondary packaging (e.g., carrier, package, blister or container) that is compartmentalized to receive one or more primary packaging containers (e.g., vials, tubes, and the like as described above), each of the container(s) comprising one of the separate elements to be used in a method described herein including a morphine formulations. Suitable primary packaging containers include, for example, vials, syringes, ampoules, bottles, cartridges, carpules and i.v. bags or pouches. The containers can be formed from a variety of materials such as glass or plastic.

A kit typically may comprise one or more additional containers, each with one or more of various materials (such as devices) desirable from a commercial and user standpoint for a morphine formulations described herein. Non-limiting examples of such materials include, but not limited to, buffers, diluents, filters, needles, syringes; adaptors, waste receptacles, and/or labels listing contents and/or instructions for use, and package inserts with instructions for use associated with a morphine formulation. A set of instructions will also typically be included.

A label can be on or associated with the secondary packaging. A label can be on a secondary packaging when letters, numbers or other characters forming the label are attached, molded or etched into the container itself; a label can be associated with a secondary packaging when it is present within a receptacle or carrier that also holds the primary packaging container, e.g., as a package insert. A label can be used to indicate that the contents are to be used for a specific therapeutic application. The label can also indicate directions for use of the contents, such as in the methods described herein.

Certain Definitions

Unless defined otherwise, all technical and scientific terms used herein have the same meanings as commonly understood by one of ordinary skill in the art. Although any methods and materials similar or equivalent to those described herein can be used in the practice or testing of embodiments described herein, certain preferred methods, devices, and materials are now described.

As used herein and in the appended claims, the singular forms "a", "an", and "the" include plural reference unless the context clearly dictates otherwise. Thus, for example, reference to "an excipient" is a reference to one or more excipients and equivalents thereof known to those skilled in the art, and so forth.

The term "about" is used to indicate that a value includes the standard level of error for the device or method being employed to determine the value. The use of the term "or" in the claims is used to mean "and/or" unless explicitly indicated to refer to alternatives only or the alternatives are mutually exclusive, although the disclosure supports a definition that refers to only alternatives and to "and/or." The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

"Optional" or "optionally" may be taken to mean that the subsequently described component, structure, event or circumstance may or may not occur, and that the description includes instances where the events occurs and instances where it does not.

As used herein, the term "therapeutic" means an agent utilized to treat, combat, ameliorate, prevent or improve an unwanted condition or disease of a patient. In some embodiments, a therapeutic agent such as morphine is directed to the treatment and/or the amelioration of, reversal of, or stabilization of the pain described herein.

"Administering" when used in conjunction with a therapeutic means to administer a therapeutic systemically or locally, as directly into or onto a target tissue, or to administer a therapeutic to a patient whereby the therapeutic positively impacts the tissue to which it is targeted. Thus, as used herein, the term "administering", when used in conjunction with a morphine formulation, can include, but is not limited to, providing a morphine formulation into or onto the target tissue; providing a morphine formulation systemically to a patient by, e.g., injectable administration whereby the therapeutic reaches the target tissue or cells. "Administering" a composition may be accomplished by injection administration or by other methods alone or in combination with other known techniques.

The term "animal" as used herein includes, but is not limited to, humans and non-human vertebrates such as wild, domestic and farm animals. As used herein, the terms "patient," "subject" and "individual" are intended to include living organisms in which certain conditions as described herein can occur. Examples include humans, monkeys, cows, sheep, goats, dogs, cats, mice, rats, and transgenic species thereof. In a preferred embodiment, the patient is a primate. In certain embodiments, the primate or subject is a human. In certain instances, the human is an adult. In certain instances, the human is child. In further instances, the human is under the age of 12 years. In certain instances, the human is elderly. In other instances, the human is 60 years of age or older. Other examples of subjects include experimental animals such as mice, rats, dogs, cats, goats, sheep, pigs, and cows. The experimental animal can be an animal model for a disorder that results in pain systems. A patient can be a human suffering from pain, in various degrees or from etiological forms.

By "pharmaceutically acceptable", it is meant the carrier, diluent or excipient must be compatible with the other ingredients of the formulation and not deleterious to the recipient thereof.

The term "pharmaceutical composition" or "pharmaceutical formulation" shall mean a composition comprising at least one active ingredient, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

A "therapeutically effective amount" or "effective amount" as used herein refers to the amount of active compound or pharmaceutical agent that elicits a biological or medicinal response in a tissue, system, animal, individual or human that is being sought by a researcher, veterinarian, medical doctor or other clinician, which includes one or more of the following: (1) preventing the disease; for example, preventing a disease, condition or disorder in an individual that may be predisposed to the disease, condition or disorder but does not yet experience or display the pathology or symptomatology of the disease, (2) inhibiting the disease; for example, inhibiting a disease, condition or disorder in an individual that is experiencing or displaying the pathology or symptomatology of the disease, condition or disorder (i.e., arresting further development of the pathology and/or symptomatology), and (3) ameliorating the disease; for example, ameliorating a disease, condition or disorder in an individual that is experiencing or displaying the pathology or symptomatology of the disease, condition or disorder (i.e., reversing the pathology and/or symptomatology). As such, a non-limiting example of a "therapeutically effective amount" or "effective amount" of a composition of the present disclosure may be used to inhibit, block, or reverse pain or to effectively induce anesthesia.

The terms "treat," "treated," "treatment," or "treating" as used herein refers to both therapeutic treatment in some embodiments and prophylactic or preventative measures in other embodiments, wherein the object is to prevent or slow (lessen) an undesired physiological condition, disorder or disease, or to obtain beneficial or desired clinical results. For the purposes described herein, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment. A prophylactic benefit of treatment includes prevention of a condition, retarding the progress of a condition, stabilization of a condition, or decreasing the likelihood of occurrence of a condition. As used herein, "treat," "treated," "treatment," or "treating" includes prophylaxis in some embodiments.

EXAMPLES

Example 1

Oxygen and pH on Stability

A forced degradation study was performed to determine the optimum pH for a 10 mg/mL morphine sulfate injectable formulation and the impact of oxygen on that stability.

Figure 2:
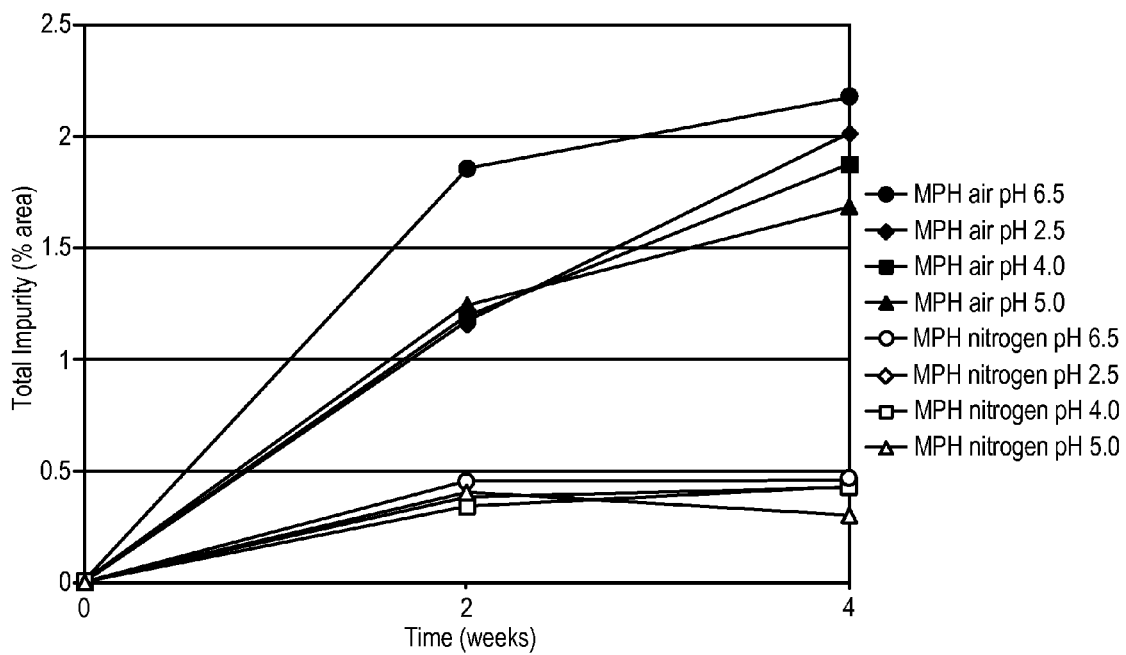
FIG. 2: Total impurities results by UPLC for 10 mg/mL morphine sulfate solution having pH 2.5, 4.0, 5.0 or 6.5 prepared under inert (nitrogen) or air conditions stored at accelerated conditions (40° C./75% RH) for 4 weeks.
Figure 3:
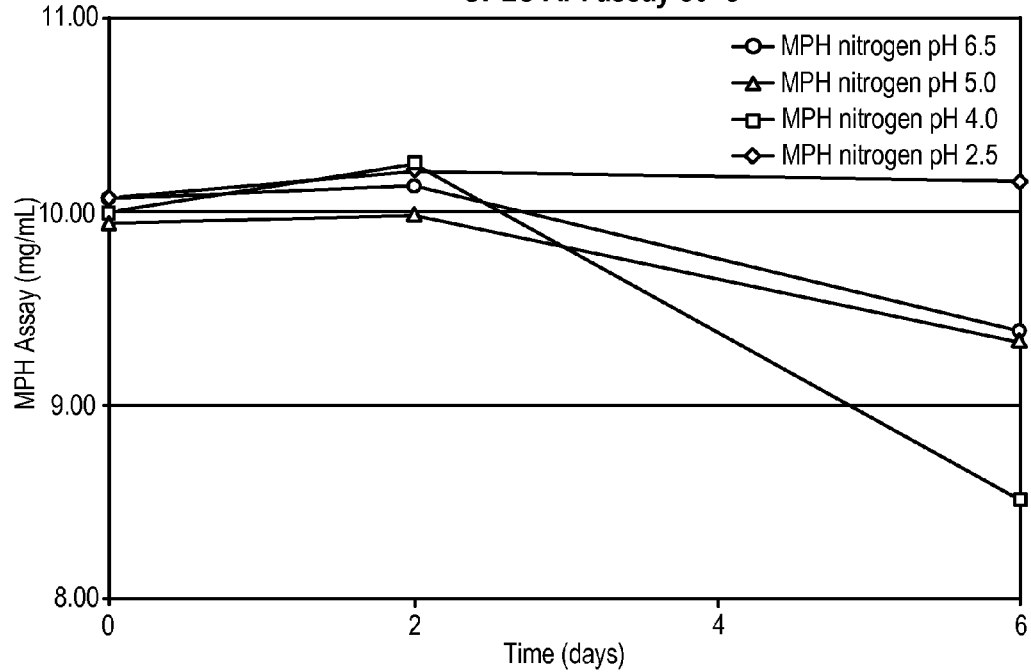
FIG. 3: Morphine content results by UPLC for 10 mg/mL morphine sulfate solution having pH 2.5, 4.0, 5.0 or 6.5 prepared under inert (nitrogen) conditions at storage condition of 80° C. for 6 days.

Morphine sulfate solutions at 10 mg/mL were formulated under 2 different conditions: one under inert conditions (nitrogen); the other under air. The pH of each solution was adjusted to 2.5, 4.0, 5.0 or 6.5. The solutions were individually stored in 10 mL amber vials, to prevent morphine dimerization from light. A set of samples were stored in 1) 6 days in an oven at 80° C., and another set stored at 2) 4 weeks in a climatic room at 40° C. Morphine and impurities were assessed by UPLC. FIGS. 1 to 3 depict the results of the pH and oxygen stability studies.

FIGS. 1 and 2 show that the morphine solutions prepared under inert conditions are more stable when stored at 80° C. (FIG. 1) and 40° C. (FIG. 2). FIG. 1 shows that all morphine solutions prepared under air had higher total impurities than solutions prepared under inert conditions when stored at 80° C. for six days. With respect to pH, the solution prepared under air at pH 2.5 showed the highest degradation whereas the lowest degradation exhibited by the solution prepared under air at pH 5.0. In inert conditions, morphine solutions at pH 5.0 also exhibited the least amount of degradation at 80° C. At the 40° C. storage condition (FIG. 2), morphine solutions prepared under air also showed higher total impurities than solutions prepared under inert conditions. Total impurities are also lowest when the formulation pH is 5.0 in both air and inert conditions.

Morphine was also assayed via UPLC in the inerted set of morphine solutions stored at 80° C. for six days (FIG. 3). FIG. 3 shows that, under nitrogen, the amount of morphine in the formulation is highest at pH 2.5. A significant decrease of the morphine (3% in 6 days at 80° C.) is observed at pH 6.5 and some decrease is observed at pH 5.0 and pH 4.0.

The results indicate that the preparation of the solutions under nitrogen minimizes the oxidation effect and prevent an increased degradation. The results also indicate pH 5.0 is an optimal one according to the pH and oxygen stability studies. pH 5.0 morphine solutions showed least amount of total impurities (FIGS. 1 and 2). While the morphine formulation at pH 2.5 showed less morphine decrease than at pH 5 at 80°

C. (FIG. 3), it is known that a pH of 2.5 is very acidic and can cause pain at the injection site. A formulation pH of about 5.0, as provided herein, is closer to the physiological pH. Accordingly the formulations at pH 5.0 maintain the fine balance of having a pH closer to physiological pH (thereby reducing pain at the injection site due to a low pH, e.g., 2.5); of having lower total impurities during storage; and of having higher morphine content compared to formulations with pH of 4.0 and 6.5 (FIG. 2).

Example 2

Stability of Morphine/NaCl Formulations

The stability of morphine sulfate/NaCl formulations were evaluated under ICH long term storage conditions at 25° C./65% Relative Humidity (RH) and at the accelerated storage condition of 40° C./75% RH for 6 months. Three dosage forms were tested: 2 mg/mL, 5 mg/mL and 10 mg/mL in formulations according to the following table:

|  | Strength Composition/mL | | |
| --- | --- | --- | --- |
|  | 2 mg/mL | 5 mg/mL | 10 mg/mL |
| Morphine | 2 mg | 5 mg | 10 mg |
| Sodium chloride | 9 mg | 9 mg | 8.8 mg |
| Water for injection | s.q.f 1 mL | s.q.f 1 mL | s.q.f 1 mL |

NaCl was added to the morphine formulations at defined quantities to produce compatible osmolality conditions. The formulations were adjusted to pH 5.0 by HCl or NaOH and filled into 1.25 mL glass syringes (Hypak™, Becton Dickinson & Co.) with a stopper. The effect of nitrogen compounding and filling was evaluated: two levels of Oxygen Partial Pressure (fully inerted "N2" and partially inerted "SemiN2") were tested alongside with a compounding and filling under air (non-inerted "Air"). The effect of steam sterilization was also studied (autoclaved "A" and not autoclaved "NonA").

Figure 4:
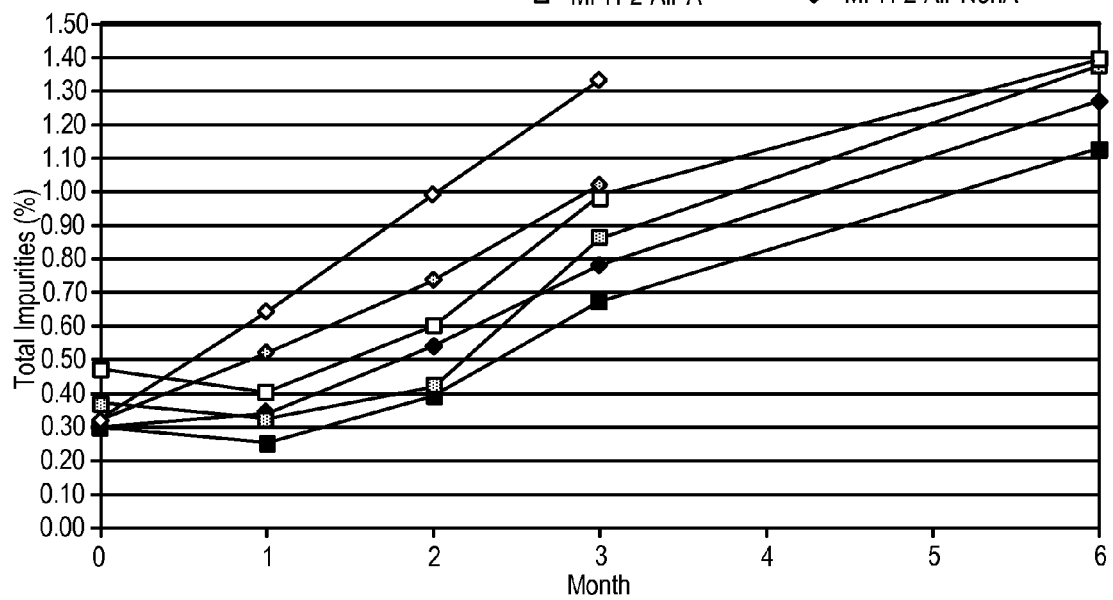
FIG. 4: Total impurities results by UPLC for 2 mg/mL morphine sulfate/NaCl formulation stored 6 months at accelerated conditions (40° C./75% RH) for different process configurations [Oxygen: N2 (fully inert), SemiN2 (partially FIG. 5: Pseudomorphine content by UPLC for Morphine sulfate/NaCl formulation 2, 5 and 10 mg/mL, fully inerted and autoclaved stored at accelerated conditions (40° C./75% RH) for 6 months.

FIG. 4 presents the levels of the total impurities content at the 2 mg/mL concentration at 6 month storage at 40° C./75% RH. After 6 month storage at 40° C./75% RH (FIG. 4) and at 25° C./60% RH and complementary studies at 60° C. and 80° C., it appeared that fully inerted (dark symbols) and autoclaved formulations (squares) gave the best results in terms of assay stability, total and individual impurity content and pH stability.

Figure 5:
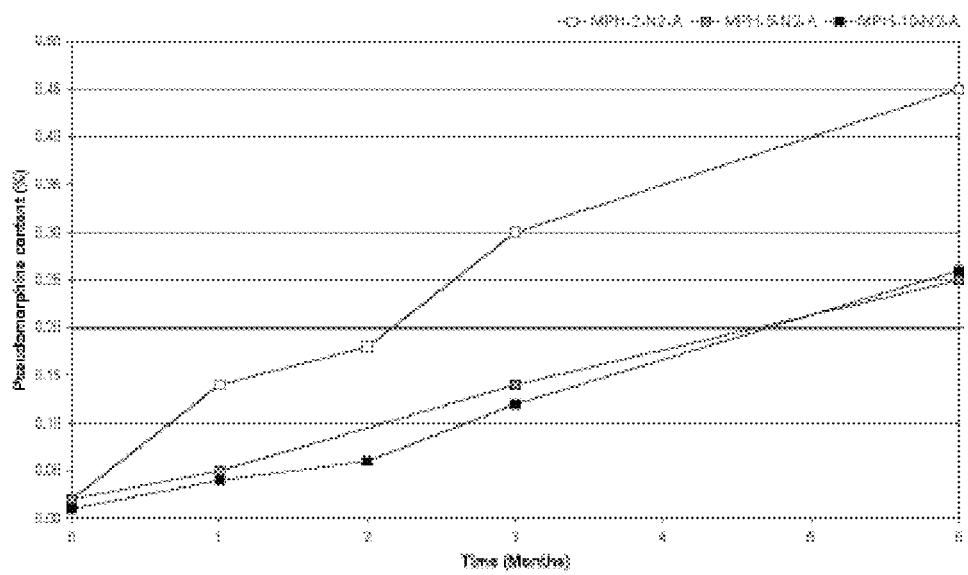
Figure 6:
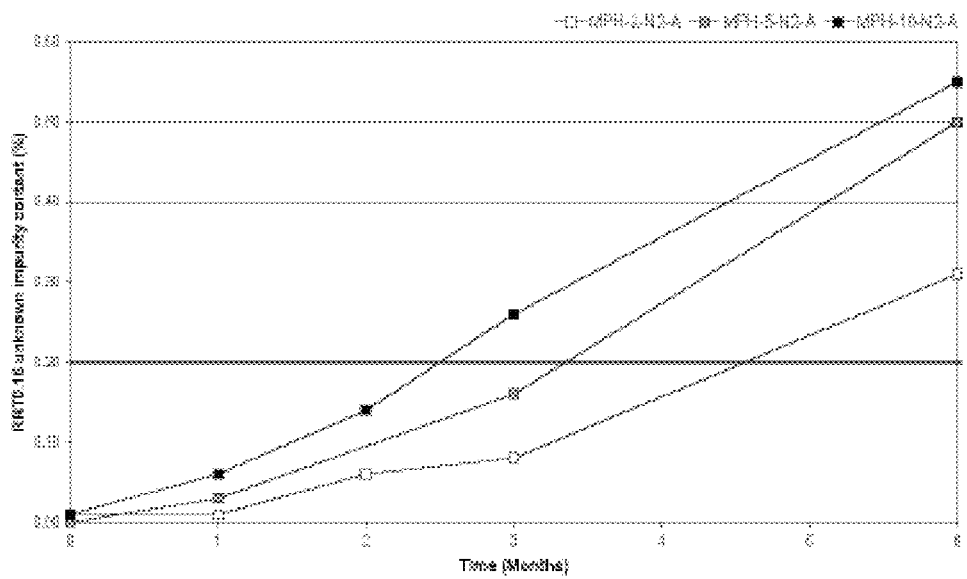
FIG. 6: Relative Retention time 0.16 Unknown Impurity content by UPLC of Morphine sulfate/NaCl formulation 2, 5 and 10 mg/mL, fully inerted and autoclaved stored at 40° C./75% RH) for 6 months.

Impurities were also individually assessed. At 6 month storage at 40° C./75% RH, the results showed individual contents greater than expected specifications (NMT 0.20%), mainly for pseudomorphine and an unknown impurity (identified at the relative retention time of 0.16). The increase of the pseudomorphine impurity is presented in the FIG. 5 for the 3 strengths 2, 5 and 10 mg/mL, in the fully inerted "N2" and autoclaved "A" configuration. FIG. 6 shows the increase of the RRT 0.16 unknown impurity for the 3 strengths 2, 5 and 10 mg/mL, in the fully inerted "N2" and autoclaved "A" configuration. It is contemplated that the formulation of those 2 degradants is promoted by oxidative and/or hydrolysis reactions.

Example 3

Stability of Various Morphine and Excipient Formulations

The results from Example 2 led to examination of additional morphine formulations. The aim was to add excipients to prevent the formation of these degradants that appeared out of specification in the previous example. Thus, a forced degradation study and an accelerated stability study were performed on different new formulations of morphine sulfate formulations at 2 mg/mL, all adjusted at a pH of about 5.0 and prepared under nitrogen. The various formulations included antioxidants (metabisulfite), buffer system (citric acid/sodium citrate) and chelating agent and complement (EDTA/$CaCl_2$) without steam sterilization. The formulations were prepared, filled into 1.25 mL glass syringes (Hypak™, Becton Dickinson & Co.) with a stopper and were placed at 40° C./75% RH for 1 month, and 80° C. for 14 days for assessing stability. The below table summarizes the different formulations tested and the results observed.

| Composition | Objective | Results |
| --- | --- | --- |
| Sodium metabisulfite + pH adjustment (MPH-2-PH-NonA) | Test antioxidant properties of sulfites | decrease of pH decrease of API increase of impurity level above specification |
| Sodium metabisulfite + sodium citrate/citric acid buffer (MPH-2-TAM-NonA) | Test antioxidant properties of sulfites Test buffering and antioxidant properties of citric acid/sodium citrate | decrease of API increase of impurity level above specification |
| Sodium metabisulfite + sodium citrate/citric acid + chelating agent/complement (MPH-2-CHE-NonA) | Test antioxidant properties of sulfites Test buffering and antioxidant properties of citric acid/sodium citrate Test effect of chelating agent on oxidation reactions | decrease of API increase of impurity level above specification |
| Chelating agent/complement + pH adjustment (MPH-2-PH-SS-NonA) | Test effect of chelating agent on oxidation reactions | increase of pH (at 80° C.) |
| Sodium citrate/citric acid + chelating agent/complement (MPH-2-TAM-SS-NonA) | Test buffering and antioxidant properties of citric acid/sodium citrate Test effect of chelating agent on oxidation reactions | pH and API stable lower level of impurities |

Figure 7:
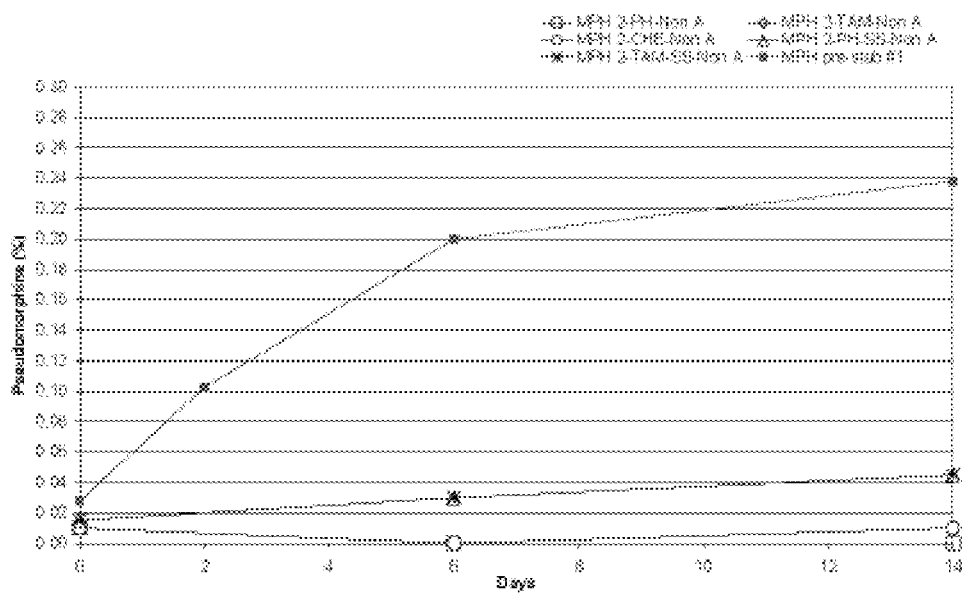
FIG. 7: Pseudomorphine content by UPLC of various 2 mg/mL Morphine sulfate formulations as described in Example 3, fully inerted and non-autoclaved stored at 80° C. for 14 days.
Figure 8:
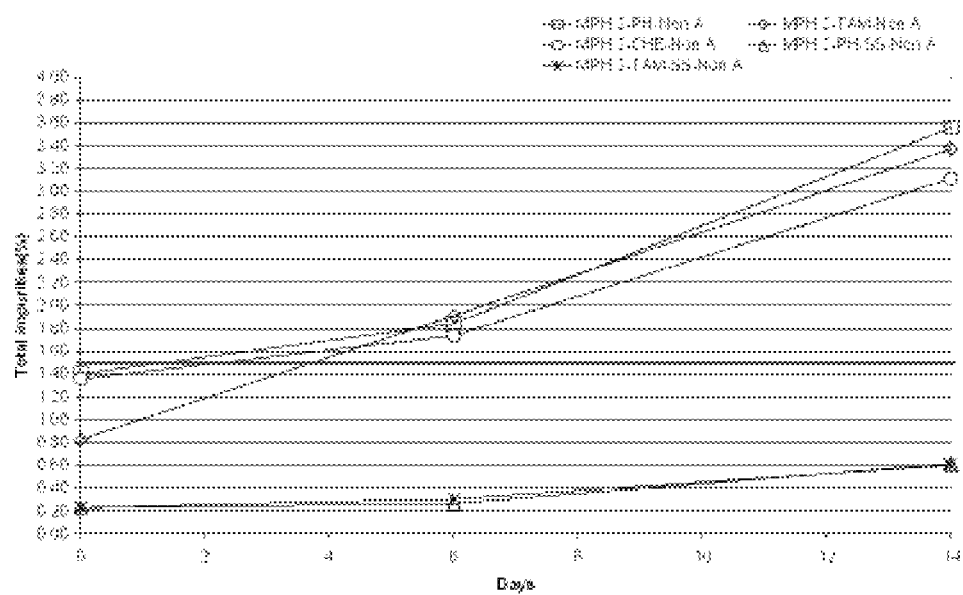
FIG. 8: Total impurities content by UPLC of various 2 mg/mL Morphine sulfate formulations as described in Example 3, fully inerted and non-autoclaved stored at 80° C. for 14 days.

FIG. 7 depicts the above five formulations presented lower content of pseudomorphine impurity after 14 days at 80° C.

than the first developed formulation of Morphine/NaCl (MPH pre-stab #1). The formulations with metabisulfite had lower pseudomorphine impurity than formulations without metabisulfite. However for these later formulations the level of the pseudomorphine impurity only reached 0.05% after 14 days at 80° C. In contrast, after 14 days at 80° C. storage condition, the total impurities content for the three formulations with metabisulfite was far above the specification limit (1.5%), whereas the two formulations without metabisulfite presented low total impurities levels (FIG. 8). Further, while formulations containing metabisulfite, a known antioxidant, had reduced levels of the pseudomorphine degradant, the results show the rise of many other degradants making this metabisulfite not suitable for improving the stability of morphine formulations.

Figure 9:
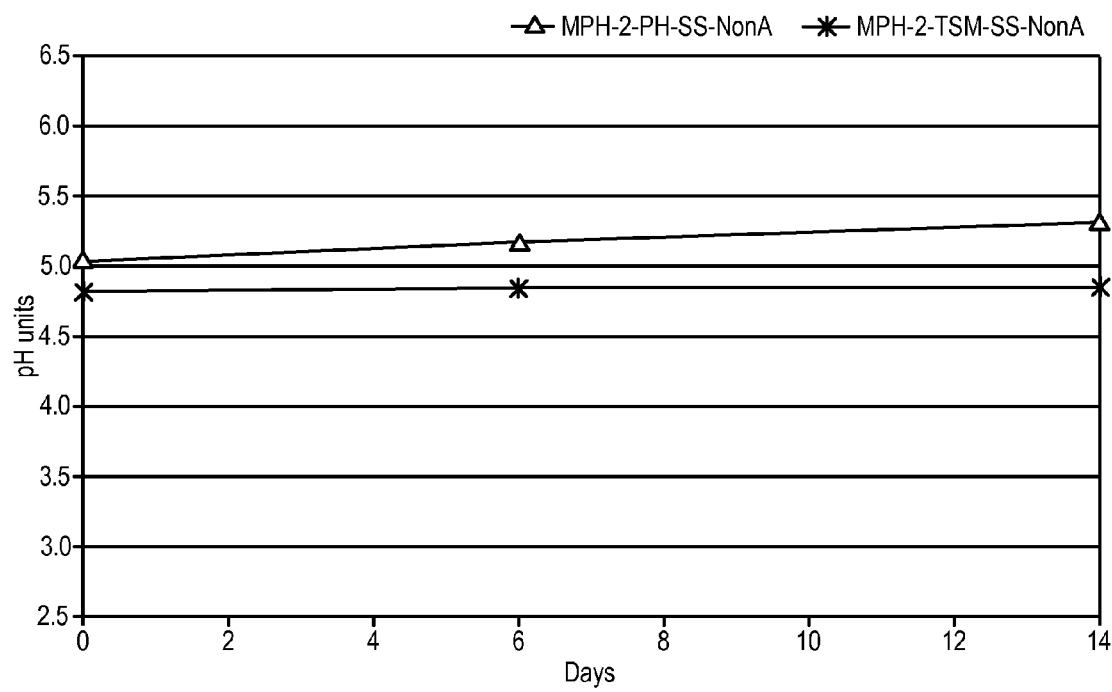
FIG. 9: Comparison of two 2 mg/mL Morphine sulfate formulations (+chelating agents and pH adjusted; +chelating agents and +buffer system), fully inerted and non-autoclaved stored at 80° C. for 14 days—pH assay.

The two non-sulfite formulations were examined on pH behavior at 80° C. As shown by the FIG. 9, the pH trend of the formulation with chelating agent/complement and pH adjustment increases regularly over the 14 days storage period (+0.3%). The non-sulfite formulation with the addition of the buffer system (MPH-2-TAM-SS-NonA) had a more stable pH trend. The results show that the formulation with a buffer system (e.g., citric acid/sodium citrate) and chelating agent/complement (EDTA and calcium chloride) was the most stable formulation after 14 days at 80° C. as well as after 1 month stability at 40° C./75% RH.

The effect of steam sterilization was also tested. It was observed in the non-sulfite formulation having the buffer system and chelating agent/complement (MPH-2-TAM-SS-NonA) after 14 days at 80° C., that the unknown impurity at RRT 0.16 increased at a greater rate for the autoclaved form than the non-autoclaved form. Thus, the results in this example suggest that autoclaving the morphine formulations is not beneficial for stability.

Example 4

Exemplary Morphine Formulations and their Preparation

Various morphine formulations comprising a buffer system and chelating agent/complement were prepared according to the following table.

The manufacturing process was performed under nitrogen. For manufacturing a batch of one of the above exemplary morphine formulations, the morphine, citric acid, EDTA, calcium chloride, sodium citrate and sodium chloride were weighed in scaled up quantities. A formulation tank held and agitated water for injection for compounding the drug and the various excipients. In the tank, each component was individually added and allowed to dissolve to completion (e.g., at least 5 to 10 minutes) prior to the addition of the next component. Morphine was added last. After the last addition, the tank was filled with water for injection at sufficient quantity for (s.q.f) the specified morphine concentration and agitated for a period of time to homogeneity.

Content uniformity of the formulations was assessed at various timepoints during the final agitation at the top, middle and bottom sections of the formulation tank. The morphine formulations were then filtered twice through 0.22 μm filters in the manufacturing process. After the second filtration, the formulations were filled into the primary packaging container.

Example 5

Accelerated Stability Studies with Primary and Standard Secondary Packaging

The 2 mg/mL and 10 mg/mL morphine formulations of Example 4 were evaluated under ICH accelerated conditions at 40° C./75% RH for 6 months in 1.25 mL glass syringes (Hypak™) with a stopper. The syringes containing the morphine formulations were placed in a secondary blister packaging of PET (polyethylene terephthalate) material with a paper lid backing.

Results of the stability assay after 6 months storage at 40° C./75% RH revealed that morphine content in stayed within specification parameters (NMT±10% change) for both concentrations. The assay values stayed stable in the 2 mg/mL formulation while the assay values for morphine decreased slightly in the 10 mg/mL formulation but remained within specification. Similarly, total impurities level increased regularly over time but stayed below the specification (NMT 1.5%) for both strengths. pH values also remained stable over the 6 month storage period.

Figure 10:
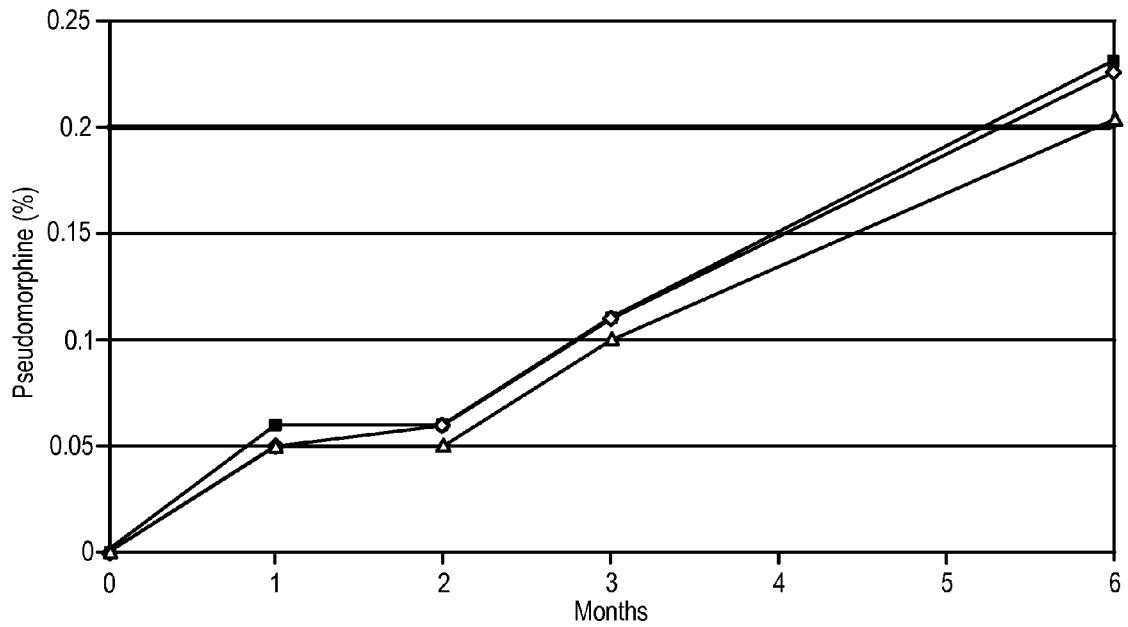
FIG. 10: Pseudomorphine content by UPLC of 2 mg/mL Morphine sulfate formulation from Example 4 stored 6 months at accelerated conditions (40° C./75% RH).

With respect to individual impurities, pseudomorphine appeared after 1 month storage period and increased regularly over the storage period in both the 2 mg/mL and 10 mg/mL morphine formulations. At the end of 6 months storage, this impurity passed the specification limit (NMT 0.2%). FIG. 10 depicts the presence of pseudomorphine over time in the 2

|  | Morphine Formulation Strength - composition per mL | | | | |
| --- | --- | --- | --- | --- | --- |
| Material | 2 mg/mL | 4 mg/mL | 5 mg/mL | 8 mg/mL | 10 mg/mL |
| Morphine sulfphate pentahydrate | 2.00 mg | 4.00 mg | 5.00 mg | 8 mg/mL | 10.00 mg |
| Sodium chloride | 8.40 mg | 8.40 mg | 7.50 mg | 7.50 mg | 7.50 mg |
| Sodium citrate dihydrate | 2.30 mg | 2.30 mg | 3.45 mg | 3.45 mg | 3.45 mg |
| Citric Acid monohydrate | 0.74 mg | 0.74 mg | 1.11 mg | 1.11 mg | 1.11 mg |
| Disodium edetate dihydrate | 0.111 mg | 0.111 mg | 0.111 mg | 0.111 mg | 0.111 mg |
| Calcium chloride dihydrate | 0.053 mg | 0.053 mg | 0.053 mg | 0.053 mg | 0.053 mg |
| Water for injection | s.q.f 1 mL | s.q.f 1 mL | s.q.f 1 mL | s.q.f 1 mL | s.q.f 1 mL | mg/mL formulation of three different batches. The pseudomorphine increase was at a greater rate in the 10 mg/mL formulation and reached the specification limit earlier.

Example 6

Accelerated Stability Studies with Primary and Oxygen Barrier Secondary Packaging In order to improve the stability and shelf life of the morphine formulation of Example 4, an oxygen barrier secondary packaging was developed.

The alternative blister packaging included a thermoformed transparent shell made of a multilayer plastic film including PET and EVOH (Ethylene vinyl alcohol) (bottom web), and a heat sealed lidding material made of paper, PET and aluminum foil (top web). The EVOH layer of the bottom web presents a very low permeability to oxygen molecules and the aluminum foil is impermeable to any gas. Thus, this blister packaging restricts the atmospheric oxygen re-entry into the secondary packaging. Moreover an oxygen absorber was placed inside the blister. This absorber included an iron powder formula filled in a canister made of HDPE plastic and functioned to absorb any oxygen present in the secondary packaging. The primary packaging container, i.e., syringe, containing the morphine formulation was then placed in this alternative blister packaging.

Accelerated conditions at 40° C./75% RH for 6 months were assessed similarly to the previous example. For the both strengths, the morphine content remained stable over time and the results were compliant with the specification (90-110%). However, with the oxygen barrier secondary packaging configuration, the impurity profile, and more specifically the pseudomorphine impurity, were considerably improved. For the all batches of the both strengths, the highest result of total impurities content were very low and stayed very far below the specification limit (NMT 1.5%). The pseudomorphine content was very low and even below the limit of quantification. Results of pseudomorphine content over the 6-month storage period in accelerated conditions are presented in the following tables:

| 2 mg/mL Morphine in Oxygen Barrier Packaging - Pseudomorphine Content | | | | | |
|---|---|---|---|---|---|
| | T0 | T1 Month | T2 Months | T3 Months | T6 Months |
| Batch 1 | ND | 0.05 | 0.03 | 0.04 | 0.04 |
| Batch 2 | ND | 0.05 | 0.03 | 0.04 | 0.03 |
| Batch 3 | ND | 0.04 | 0.01 | 0.02 | 0.01 |

| 10 mg/mL Morphine in Oxygen Barrier Packaging - Pseudomorphine Content | | | | | |
|---|---|---|---|---|---|
| | T0 | T1 Month | T2 Months | T3 Months | T6 Months |
| Batch 1 | 0.02 | 0.02 | 0.03 | 0.03 | 0.03 |
| Batch 2 | 0.02 | 0.02 | 0.02 | 0.03 | 0.02 |
| Batch 3 | 0.02 | 0.02 | 0.03 | 0.02 | 0.03 |

As shown above, the pseudomorphine content also stayed far below the specification limit (NMT 0.2%). The data in the example showed that the stability results obtained on the batches packaged with the oxygen barrier packaging system show that the combination of the formulation with the buffer and chelating systems, the manufacturing process under nitrogen and the oxygen barrier packaging ensure a good preservation of the morphine formulation against oxidation reactions.

Example 7

Stability Comparison of Morphine Formulations from Example 4 in Oxygen Barrier Packaging with Marketed Morphine Formulation Products of Equal Strengths 2 mg/mL, 5 mg/mL and 10 mg/mL morphine formulations were prepared according to Example 4 and filled into 1.25 mL glass syringes (Hypak™) with a stopper and placed into the oxygen barrier secondary packaging as described in Example 6. The stability was compared with marketed morphine formulation products of equal strengths. The testing conditions and results are summarized in the following table:

| Analytical Tests | | Product Name | | | | | |
|---|---|---|---|---|---|---|---|
| | | Morphine Product on Market 2 mg/mL | Example 5 Morphine formulation with O2 barrier packaging 2 mg/mL | Morphine Product on Market 5 mg/mL | Example 5 Morphine formulation with O2 barrier packaging 5 mg/mL | Morphine Product on Market 10 mg/mL | Example 5 Morphine formulation with O2 barrier packaging 10 mg/mL |
| | | Test time point & condition | | | | | |
| | | Tested at 17 mos. Ambient conditions | Tested at 6 mos. at 40° C./75% RH | Tested at 2 mos. After expiry Ambient conditions | Tested at 6 mos. at 40° C./75% RH | Tested at 13 mos. Ambient conditions | Tested at 6 mos. at 40° C./75% RH |
| | | Expiry date | | | | | |
| | | 24 mos at 20° C.-25° C. | 24 mos at 20° C.-25° C. (proposed) | 24 mos at 20° C.-25° C. | 24 mos at 20° C.-25° C. (proposed) | 24 mos at 20° C.-25° C. | 24 mos at 20° C.-25° C. (proposed) |
| Assay of Morphine (%) | 90%-110% | 101% | 101% | 101% | 100% | 104% | 100% |
| Total Impurities (%) | NMT 1.0% | 1.7% | 0.0% | 0.7% | 0.1% | 1.1% | 0.0% |

-continued

| | | Product Name | | | | | |
|---|---|---|---|---|---|---|---|
| | | Morphine Product on Market 2 mg/mL | Example 5 Morphine formulation with O2 barrier packaging 2 mg/mL | Morphine Product on Market 5 mg/mL | Example 5 Morphine formulation with O2 barrier packaging 5 mg/mL | Morphine Product on Market 10 mg/mL | Example 5 Morphine formulation with O2 barrier packaging 10 mg/mL |
| | | | | Test time point & condition | | | |
| | | Tested at 17 mos. Ambient conditions | Tested at 6 mos. at 40° C./75% RH | Tested at 2 mos. After expiry Ambient conditions | Tested at 6 mos. at 40° C./75% RH | Tested at 13 mos. Ambient conditions | Tested at 6 mos. at 40° C./75% RH |
| | | | | Expiry date | | | |
| Analytical Tests | | 24 mos at 20° C.-25° C. | 24 mos at 20° C.-25° C. (proposed) | 24 mos at 20° C.-25° C. | 24 mos at 20° C.-25° C. (proposed) | 24 mos at 20° C.-25° C. | 24 mos at 20° C.-25° C. (proposed) |
| Codeine Impurity | NMT 0.2% | 0.06% | 0.05% | 0.06% | 0.04% | 0.07% | 0.05% |
| Pseudomorphine impurity | NMT 0.2% | ND | 0.04% | 0.23% | 0.03% | ND | 0.03% |
| Oripavine impurity | NMT 0.2% | ND | ND | ND | ND | ND | ND |
| 10-hydroxymorphine impurity | NMT 0.2% | 0.15% | 0.04% | 0.04% | 0.06% | 0.08% | 0.03% |
| Morphine-N-oxide | NMT 0.2% | ND | ND | ND | 0.05% | ND | ND |
| Normorphine impurity | NMT 0.2% | ND | ND | ND | ND | ND | ND |
| Morphinone impurity | NMT 0.2% | ND | ND | 0.07% | ND | ND | ND |
| Apomorphine impurity | NMT 0.2% | ND | — | ND | — | ND | ND |
| Unknown impurity | NMT 0.2% | RRT (%) 0.096 (0.38%) 0.144 (0.12%) 0.165 (0.38%) 0.182 (0.08%) 0.213 (0.05%) 0.284 (0.15%) 0.391 (0.24%) 0.434 (0.08%) | RRT (%) 0.16 (0.02%) | RRT (%) 0.120 (0.21%) 1.102 (0.06%) | RRT (%) 0.16 (0.03%) | RRT (%) 0.097 (0.10%) 0.144 (0.15%) 0.166 (0.19%) 0.185 (0.10%) 0.284 (0.16%) 0.394 (0.22%) | RRT (%) 0.16 (0.02%) |

As shown above, the morphine formulations of Example 5 in oxygen barrier secondary packaging had much better stability than the marketed morphine products of comparable strengths even when the marketed morphine products were stored at ambient conditions while the morphine formulations of Example 5 were stored in accelerated (40° C./75% RH) conditions for 6 months which is known to be indicative of 2 years at room temperature. The impurity assays show that all of the marketed morphine products were out of specification limits for either total and/or a particular impurity while the morphine formulations of Example 5 were completely within specification with very low levels of pseudomorphine (far below 0.1%) and only one unknown impurity RRT 0.16 at 0.02-0.03%. The marketed morphine product at 2 mg/mL presented a high level of total impurities (1.7%) and was out of specification (according to ICH Q3B guidance) for two unknown impurities; other unknown impurities were found significantly greater than 0.1%. The marketed morphine product at 5 mg/mL showed unacceptable pseudomorphine and unknown impurity levels. Finally, the marketed morphine product at 10 mg/mL, analyzed at about half of its shelf life had a high total impurity level and up to 6 unknown impurities, 4 of which being very close or that could be rounded to 0.2%; this indicates that this product is unlikely to meet stability acceptance criteria after two years. The results in this example demonstrate the increased purity and stability of exemplary morphine formulations described herein.

Example 8

Additional Long-Term Stability Studies of 10 Mg/mL Morphine Formulations with Primary and Oxygen Barrier Secondary Packaging Long-term stability of 10 mg/mL morphine formulations was observed in ambient, intermediate and accelerated conditions. 10 mg/mL morphine formulations were prepared according to Example 4 and filled into 1.25 mL glass syringes (Hypak™) with a stopper and placed into the oxygen barrier secondary packaging as described in Example 6. The packaged syringes containing the 10 mg/mL morphine formulations were stored at ambient conditions (25° C./60% RH) for a duration of 24 months or the 24-month equivalent duration in intermediate (35° C./65% RH, for 12 months) and accelerated conditions (40° C./75% RH, for six months). At various points during the storage period, the morphine formulations were assessed similarly to the previous examples.

24 Month Ambient Condition Stability Results

After 24 months storage, the morphine formulations were within specification. The stored formulations remained clear and colorless with no visible particles detected. The number of subvisible particles per syringe increased over time, but remained far below the specification limits. The pH was also stable over the storage period.

Morphine content, assayed by UPLC, ranged from 98.6%-101.0% during the storage period and was within specification limits. The content of any individual impurity (e.g., codeine, pseudomorphine, oripavine, norphonine and morphinone as well as unknown umpurities) were detected but below the limits of quantification. These impurities as well as the sum of the impurities were therefore compliant with the impurity specifications.

The solution remained sterile after 24 months storage at ambient conditions, confirming that the primary and oxygen barrier packaging remained unaltered after the storage period. Endotoxin content after 24 months storage was also compliant with specification.

The syringe also remained functional after 24 months from expel testing.

12-Month Intermediate and Six-Month Accelerated Stability Results

Results were similar in the storage stability studies in the 12-month intermediate and six-month accelerated stability studies. For these two conditions, all parameters were within specification. Qualitatively, morphine formulations remained clear and colorless with no visible particles detected. Known and unknown impurities were compliant under the specified limits. No signficant change occurred in these two conditions.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An injectable pharmaceutical formulation comprising per mL:
    (a) from about 2 mg to about 10 mg of morphine sulfate or a hydrate thereof;
    (b) sodium chloride;
    (c) a buffering system comprised of a buffering agent in an amount which provides a molar ratio of morphine sulfate to the buffering agent from about 0.4 to about 1.3 and is in an amount sufficient to provide a pH of about 5 to the formulation and a conjugate base to the buffering agent;
    (d) disodium edetate or a hydrate thereof;
    (e) calcium chloride or a hydrate thereof; and
    (f) water for injection.

2. The formulation of claim 1, comprising
    (a) from about 4 mg and 10 mg of morphine sulfate or a hydrate thereof; and
    (c) a buffering agent in an amount which provides a molar ratio of morphine sulfate to the buffering agent from about 0.4 to 0.8 and is in an amount sufficient to provide a pH of about 5 to the formulation.

3. The formulation of claim 1, wherein the buffering agent has anti-oxidative properties.

4. The formulation of claim 1, wherein the buffering system comprises citric acid monohydrate and sodium citrate dihydrate.

5. The formulation of claim 1, wherein the formulation is stable at 80° C. for at least 14 days.

6. The formulation of claim 1, wherein the formulation is stable at 40° C. and 75% Relative Humidity for at least three months.

7. The formulation of claim 1, wherein the formulation is stable at 25° C. and 60% Relative Humidity for at least 12 months.

8. A pharmaceutical formulation comprising per mL:
    (a) from about 2 mg to about 10 mg of morphine sulfate pentahydrate;
    (b) from about 7 mg to about 9 mg of sodium chloride;
    (c) from about 2 mg to about 4 mg of sodium citrate dihydrate;
    (d) from about 0.7 to about 1.2 mg of citric acid monohydrate;
    (e) from about 0.1 to about 0.15 mg of disodium edetate dihydrate;
    (f) from about 0.04 to about 0.06 mg calcium chloride dihydrate; and
    (g) water for injection.

9. The formulation of claim 8, wherein the formulation comprises
    (a) about 2 mg morphine sulfate pentahydrate;
    (b) about 8.4 mg of sodium chloride;
    (c) about 2.3 mg of sodium citrate dihydrate;
    (d) about 0.74 mg of citric acid monohydrate;
    (e) about 0.111 mg of disodium edetate dihydrate;
    (f) about 0.053 mg calcium chloride dihydrate; and
    (g) water for injection.

10. The formulation of claim 8, wherein the formulation comprises
    (a) about 4 mg morphine sulfate pentahydrate;
    (b) about 8.4 mg of sodium chloride;
    (c) about 2.3 mg of sodium citrate dihydrate;
    (d) about 0.74 mg of citric acid monohydrate;
    (e) about 0.111 mg of disodium edetate dihydrate;
    (f) about 0.053 mg calcium chloride dihydrate; and
    (g) water for injection.

11. The formulation of claim 8, wherein the formulation comprises
    (a) about 5 mg morphine sulfate pentahydrate;
    (b) about 7.5 mg of sodium chloride;
    (c) about 3.45 mg of sodium citrate dihydrate;
    (d) about 1.11 mg of citric acid monohydrate;
    (e) about 0.111 mg of disodium edetate dihydrate;
    (f) about 0.053 mg calcium chloride dihydrate; and
    (g) water for injection.

12. The formulation of claim 8, wherein the formulation comprises
    (a) about 8 mg morphine sulfate pentahydrate;
    (b) about 7.5 mg of sodium chloride;
    (c) about 3.45 mg of sodium citrate dihydrate;

(d) about 1.11 mg of citric acid monohydrate;
(e) about 0.111 mg of disodium edetate dihydrate;
(f) about 0.053 mg calcium chloride dihydrate; and
(g) water for injection.

13. The formulation of claim 8, wherein the formulation comprises
    (a) about 10 mg morphine sulfate pentahydrate;
    (b) about 7.5 mg of sodium chloride;
    (c) about 3.45 mg of sodium citrate dihydrate;
    (d) about 1.11 mg of citric acid monohydrate;
    (e) about 0.111 mg of disodium edetate dihydrate;
    (f) about 0.053 mg calcium chloride dihydrate; and
    (g) water for injection.

14. The formulation of claim 1, wherein the formulation is stored in a glass or plastic container.

15. The formulation of claim 14, wherein the glass or plastic container is a prefilled syringe or a vial.

16. The formulation of claim 1, wherein the formulation is stored in a glass container which is stored in a secondary container having reduced permeability to oxygen and further comprising an oxygen scavenger.

17. The formulation of claim 16, wherein the formulation is stable at 40° C. and 75% Relative Humidity for at least six months.

18. The formulation of claim 16, wherein the formulation is stable at 25° C. and 60% Relative Humidity for at least 24 months.

19. A kit comprising
    (a) a pre-filled syringe comprising a morphine formulation of claim 8; and
    (b) a secondary container having reduced permeability to oxygen and further comprising an oxygen scavenger.

20. A pharmaceutical formulation comprising:
    a) morphine, or a salt thereof, or a hydrate thereof;
    b) an isotonic agent;
    c) a buffering agent with anti-oxidative properties;
    d) a chelating agent;
    e) a complement to a chelating agent; and
    (f) water;
    wherein the isotonic agent is selected from sodium chloride, calcium chloride, potassium chloride, sodium bicarbonate, sodium lactate, Ringer's solution, dextrose, lactose, mannitol, glucose, glycerine, dextran, Normosol R, saline, Hartmann's solution, and mixtures and combinations thereof.

21. The formulation of claim 20, wherein the isotonic agent is sodium chloride.

22. The formulation of claim 20, wherein the buffering agent is a di-carboxylic or tri-carboxylic acid.

23. The formulation of claim 20, wherein the buffering agent is citric acid, iso citric acid, aconitic acid, trimesic acid, propane-1,2,3-tricarboxylic acid, fumaric acid, oxalic acid, maleic acid, malonic acid, glutaric acid, succinic acid or tartaric acid, or hydrates thereof.

24. The formulation of claim 20, wherein the buffering agent is citric acid.

25. The formulation of claim 20, wherein the formulation further comprises a conjugate base to the buffering agent.

26. The formulation of claim 20, wherein the buffering agent is in an amount which provides a molar ratio of morphine to the buffering agent from about 0.4 to about 1.3.

27. The formulation of claim 20, wherein the buffering agent is in an amount which provides a molar ratio of morphine to the buffering agent from about 0.4 to about 0.8.

28. The formulation of claim 20, wherein the buffering agent forms a buffer comprised of anhydrous citric acid and hydrates thereof and anhydrous sodium citrate and hydrates thereof.

29. The formulation of claim 20, wherein the buffering agent is in an amount sufficient to provide a pH of from about 2.5 to about 6.5 to the formulation.

30. The formulation of claim 20, wherein the buffering agent is in an amount sufficient to provide a pH of from about 4.5 to about 5.5 to the formulation.

31. The formulation of claim 20, wherein the buffering agent is in an amount sufficient to provide a pH of about 5 to the formulation.

32. The formulation of claim 20, wherein the complement to chelating agent is a calcium salt.

33. The formulation of claim 20, wherein the complement to chelating agent is calcium chloride dihydrate.

34. The formulation of claim 20, wherein, the formulation provides a unit dose of morphine, or a salt thereof, or a hydrate thereof, in a concentration from about 2 mg/mL to about 15 mg/mL.

35. The formulation of claim 20 comprising per mL:
    (a) from about 2 mg to about 15 mg of morphine sulfate pentahydrate;
    (b) an isotonic agent;
    (c) a buffering agent in an amount which provides a molar ratio of morphine sulfate to the buffering agent from about 0.4 to about 1.3 and is in an amount sufficient to provide a pH of 5 to the formulation;
    (d) a chelating agent;
    (e) a complement to a chelating agent; and
    (f) water.

36. The formulation of claim 20, wherein the formulation is stable at 80° C. for at least 14 days.

37. The formulation of claim 20, wherein the formulation is stable at 40° C. and 75% Relative Humidity for at least three months.

38. The formulation of claim 20, wherein the formulation is stable at 25° C. and 60% Relative Humidity for at least 12 months.

39. The formulation of claim 20, wherein the formulation is stored in a glass or plastic container which is stored in a secondary container having reduced permeability to oxygen and further comprising an oxygen scavenger.

40. The formulation of claim 39, wherein the formulation is stable at 40° C. and 75% Relative Humidity for at least six months.

41. The formulation of claim 39, wherein the formulation is stable at 25° C. and 60% Relative Humidity for at least 24 months.

42. A kit comprising
    (a) a pre-filled syringe comprising a formulation of claim 20; and
    (b) a secondary container having reduced permeability to oxygen and further comprising an oxygen scavenger.

* * * * *